United States Patent
Nakaichi et al.

(10) Patent No.: US 7,048,692 B2
(45) Date of Patent: May 23, 2006

(54) METHOD AND APPARATUS FOR ESTIMATING AUDITORY FILTER SHAPE

(75) Inventors: Takeshi Nakaichi, Tokyo (JP); Shinichi Sakamoto, Tokyo (JP); Keisuke Watanuki, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 385 days.

(21) Appl. No.: 10/345,041

(22) Filed: Jan. 15, 2003

(65) Prior Publication Data
US 2004/0015099 A1  Jan. 22, 2004

(30) Foreign Application Priority Data

| Jan. 22, 2002 | (JP) | ............... 2002-012386 |
| Sep. 30, 2002 | (JP) | ............... 2002-286583 |
| Sep. 30, 2002 | (JP) | ............... 2002-286594 |

(51) Int. Cl.
  *A61B 5/00*  (2006.01)
(52) U.S. Cl. .................................. 600/559
(58) Field of Classification Search ............... 600/559, 600/23, 27, 28; 381/56, 73.1; 704/228; 340/384.5, 392.3
  See application file for complete search history.

(56) References Cited

U.S. PATENT DOCUMENTS

| 4,768,022 A | * | 8/1988 | Patterson | ............ 340/384.5 |
| 5,774,559 A | * | 6/1998 | Feng | ............ 381/56 |
| 5,794,188 A | * | 8/1998 | Hollier | ............ 704/228 |
| 6,109,107 A | * | 8/2000 | Wright et al. | ............ 73/585 |

FOREIGN PATENT DOCUMENTS

JP  06-327654  11/1994

OTHER PUBLICATIONS

Patterson, Roy D., "Auditory Filter Shapes Derived with Noise Stimuli", Journal of the Acoustical Society of America, vol. 59, No. 3, pp. 640-654.*

* cited by examiner

*Primary Examiner*—Max F. Hindenburg
*Assistant Examiner*—Jonathan Foreman
(74) *Attorney, Agent, or Firm*—Carrier, Blackman & Associates, P.C.; Joseph P. Carrier; William D. Blackman

(57) ABSTRACT

A method for estimating the shape of an auditory filter by finding a coefficient p of a roex (p, r) filter which is used as a model for the shape of the auditory filter is provided, which comprises the steps of: generating a tone S'; generating a masker of a notch width g and level $N_x'$ including in a notch the frequency f in which frequency characteristics of the external and middle ears of the subject are considered; transmitting to the subject a sound which superposes the masker on the tone S'; measuring the minimum notch width $g_{x-a}$ of the subject while varying the notch width g; calculating the coefficient p from an upper limit value $g_{max}$ of the notch width g suitable for the subject and estimating the shape of the auditory filter from the coefficient p calculated above and the value x corresponding to the coefficient r.

19 Claims, 10 Drawing Sheets

METHOD AND APPARATUS FOR ESTIMATING AUDITORY FILTER SHAPE

BACKGROUND OF THE INVENTION

1. Field of the Invention

The present invention relates to a method of and an apparatus for estimating the shape of a human auditory filter.

2. Description of the Relevant Art

Hearing characteristic tests for the hearing-impaired that are most frequently conducted nowadays are a hearing test (measurement of audiogram) and a speech intelligibility test. In the hearing test, it is possible to ascertain frequency characteristics of the threshold of hearing of the hearing-impaired. In the speech intelligibility test, it is possible to determine intelligibility or hearing ability of the hearing-impaired.

However, the hearing characteristics of the hearing-impaired vary with individuals. It is therefore considered that these two methods can only grasp a part of the complicated hearing characteristics.

It is generally said that the hearing-impaired have the deterioration of their frequency selectivity in addition to the deterioration of their hearing ability and the deterioration of their speech intelligibility. The frequency selectivity is the capability of distinguishing two sounds that are different in frequency. Normal hearing can distinguish two different sounds that are close in frequency, for example, 1 kHz v. 1.2 kHz, but the hearing-impaired whose frequency selectivity has deteriorated cannot distinguish these two different sounds.

When the extent of deterioration in the frequency discrimination becomes greater, it leads to deterioration of ability of discrimination of speech or deterioration of ability of discrimination of speech sound under noisy conditions. Accordingly, knowing the extent of deterioration in the frequency discrimination is very useful for a diagnosis of hearing impairments, a grasp of the hearing characteristics of the hearing-impaired, fitting of a hearing aid, etc.

In recent years, an auditory filter has been suggested as a model for expressing a mechanism of frequency analysis of the human sense of hearing. This is a method for expressing a mechanism of frequency analysis of the human inner ear by band-pass filter banks. The shape of each filter (i.e. an auditory filter) within these filter banks is usually measured using notched noise masking. A simplified method for measuring the frequency discrimination for the hearing-impaired that uses a theory of this auditory filter is disclosed in Japanese Unexamined Patent Publication No. HEI 6-327654 (1994). It is known that the shape of a human auditory filter can be modeled by a roex (p, r) filter.

In the measurement of the auditory filter by the notched noise masking, it is said that the shape of each subject's auditory filter can be measured with high accuracy. However, this measurement takes a long time and it is practically impossible for clinicians or audiologists to measure the shape of the auditory filter of each of the hearing-impaired at any time. Japanese Unexamined Patent Publication No. HEI 6-327654 (1994) suggests a method of measuring whether or not the frequency discrimination has deteriorated in a short time. According to this method, it is possible to judge whether there is any deterioration in the frequency discrimination, but is not possible to measure the extent of deterioration in the frequency discrimination, or the shape itself of the auditory filter.

Further, it is said that the shape of the auditory filter varies with the level of the input signal. It is therefore said that a masker (i.e., notched noise) whose level is about 40 dB/Hz is most suitable for the measurement of the auditory filter of people of normal hearing judging from past information. It is also said that when measured at a level higher than 40 dB/Hz, the shape of the auditory filter becomes broad. However, such a shape change in the auditory filter as seen in people of normal hearing does not always occur in all the hearing-impaired according to these levels. There is no method of measuring the shape change characteristics of the auditory filter according to each level of hearing-impairment to date.

SUMMARY OF THE INVENTION

It is therefore an object of the present invention to overcome the above-mentioned drawbacks and to provide a method of and an apparatus for accurately estimating in a short time the shape of an auditory filter effective in performing a diagnosis of the hearing impairment, grasping the hearing characteristics of the hearing-impaired, fitting of a hearing aid, and the like efficiently and correctly.

To overcome the above-mentioned drawbacks, according to the present invention, a method for estimating the shape of an auditory filter by finding a coefficient p of a roex (p, r) filter which is used as a model for the shape of the auditory filter comprises the steps of determining the threshold masking level $N_x$ based on a tone S which adds a given value x to the threshold of hearing T of a subject in frequency f, generating a tone S' which subtracts a given value a from the tone S, generating a masker of a notch width g and level $N_x$ including the frequency f in the notch, transmitting to a subject an inspection sound which superposes the masker on the tone S', measuring the minimum notch width $g_{x-a}$ of the subject while varying the notch width g, estimating the upper limit value $g_{max}$ of the notch width g suitable for the subject from the minimum notch width $g_{x-a}$, calculating a coefficient p from the upper limit value $g_{max}$, the minimum notch width $g_{x-a}$, the value x corresponding to a coefficient r and the value a, and estimating the shape of the auditory filter from the coefficient p and the value x corresponding to the coefficient r.

With this method, it is possible to precisely estimate the shape of the auditory filter effective in conducting a diagnosis of hearing impairment, grasping the hearing characteristics of the hearing-impaired, fitting of a hearing aid and the like efficiently and accurately.

It is possible to measure the minimum notch width $g_{x-a}$ of the subject using the given value x as a parameter, then estimate the upper limit value $g_{max}$ of the notch width g suitable for the subject from the minimum notch width $g_{x-a}$, calculate a coefficient p from the upper limit value $g_{max}$, the minimum notch width $g_{x-a}$, the value x corresponding to a coefficient r, and the value a, and estimate the shape of the auditory filter from the coefficient p calculated above and the given value x corresponding to the coefficient r.

In this manner, it is possible to estimate the shape of the auditory filter corresponding to the level of an input signal and to know the relationship between the input signal level and the auditory filter.

Further, in the case of measuring the threshold masking level $N_x$ and/or the minimum notch width $g_{x-a}$, it is possible to start transmission of the tone at predetermined time intervals after starting the transmission of the masker to the subject.

With this method, it is possible to easily judge the validity of response by the subject from the timing of the tone transmission and the timing of the response by the subject.

An apparatus for estimating the shape of an auditory filter (according to the present invention) by finding a coefficient p of a roex (p, r) filter which is used as a model for the shape of the auditory filter comprises a tone generation element for generating a tone of a predetermined frequency, a tone level setting element for amplifying or attenuating the tone generated at the tone generation element to a predetermined level; a noise generation element for generating noise which is not provided with a notch, a noise level setting element for amplifying or attenuating the noise generated at the noise generation element to a predetermined level, a notch width setting element for providing the noise with a notch including the frequency of the tone, a notched noise superposition element for superposing the notched noise output from the notch width setting element on a tone output from the tone level setting element, an inspection sound transmission element for transmitting to a subject an inspection sound output from the notched noise superposition element, an upper limit value calculation element for calculating the upper limit value of notch width suitable for the subject based on the notch width in the case where the subject could perceive the inspection sound, an auditory filter calculation element for calculating the coefficient p of the roex (p, r) filter based on the notch width and the upper limit value thereof and estimating the filter shape from the coefficients p, r obtained above, and an auditory filter display element for displaying the estimated filter shape.

With this apparatus, it is possible to precisely estimate the shape of the auditory filter effective in conducting a diagnosis of hearing impairment, grasping the hearing characteristics of the hearing-impaired, fitting of a hearing aid, and the like efficiently and accurately.

Further, in the case of measuring the threshold masking level $N_x$ and/or the minimum notch width $g_{x-a}$, it is possible to start transmission of the tone at predetermined time intervals after starting the transmission of the masker to the subject.

In this manner, it is possible to easily judge the validity of response by the subject from the timing of transmission of the tone and the timing of response by the subject.

Next, a method for estimating the shape of an auditory filter (according to the present invention) by finding a coefficient p of a roex (p, r) filter which is used as a model for the shape of the auditory filter comprises the steps of generating a tone S' which subtracts a given value a from a tone S which adds a given value x to the threshold of hearing T of a subject in a frequency f, generating a masker of notch width g and level $N_x$ including the frequency f in a notch, transmitting to the subject an inspection sound which superposes the masker on the tone S', measuring the minimum notch width $g_{x-a}$ of the subject while varying the notch width g, calculating the coefficient p, by applying a correction function $W_c(h)$ in which frequency characteristics in the external and middle ears of the subject are considered, from the upper limit value $g_{max}$ of the notch width g suitable for the subject from the minimum notch width $g_{x-a}$, the minimum notch width $g_{x-a}$, the value x corresponding to a coefficient r, and the value a, and estimating the shape of the auditory filter from the coefficient p calculated above and the value x corresponding to the coefficient r.

With this method, when the coefficient p of the roex (p, r) filter is calculated, it is possible to precisely estimate the shape of the auditory filter effective in performing a diagnosis of hearing impairment, a grasp of hearing characteristics of the hearing-impaired, fitting of a hearing aid and the like efficiently and accurately by applying the correction function $W_c(h)$ in which the frequency characteristics in the external and middle ears of the subject are considered.

Further, it is possible to estimate the shape of the auditory filter using the given value x as a parameter.

With this method, it is possible to estimate the shape of the auditory filter corresponding to the input signal level and know the relationship between the input signal level and the auditory filter.

It is possible to determine the threshold masking level $N_x$ based on the tone S which adds a given value x to the threshold of hearing T of the subject in a frequency f.

According to this method, it is possible to more precisely estimate the shape of the auditory filter in which frequency characteristics in the external and middle ears of the subject are considered by determining the threshold masking level $N_x$ based on the tone S which adds the given value x to the threshold of hearing T of the subject in a frequency f.

It is also possible to estimate the upper limit value $g_{max}$ of the notch width g suitable for the subject from the minimum notch width $g_{x-a}$.

In this manner, it is possible to more precisely estimate the shape of the auditory filter in which frequency characteristics in the external and middle ears of the subject are considered by estimating the upper limit value $g_{max}$ of the notch width g suitable for the subject from the minimum notch width $g_{x-a}$.

Further, in the case of measuring the threshold masking level $N_x$ and/or the minimum notch width $g_{x-a}$, it is possible to start transmission of the tone at predetermined time intervals after starting the transmission of the masker to the subject.

With this method, it is possible to easily judge the validity of response by the subject from the timing of transmission of the tone and the timing of response by the subject.

An apparatus for estimating the shape of an auditory filter (according to the present invention) by finding a coefficient p of a roex (p, r) filter which is used as a model for the shape of the auditory filter comprises a tone generation element for generating a tone of a predetermined frequency, a tone level setting element for amplifying or attenuating the tone generated at the tone generation element to a predetermined level, a noise generating element for generating noise which is not provided with a notch, a noise level setting element for amplifying or attenuating the noise generated at the noise generation element to a predetermined level, a notch width setting element for providing the noise with a notch including the frequency of the tone, a notched noise superposition element for superposing notched noise output from the notch width setting element on the tone output from the tone level setting element, an inspection sound transmission element for transmitting to a subject an inspection sound output from the notched noise superposition element, an auditory filter calculation element for calculating the coefficient p of the roex (p, r) filter by applying a correction function $W_c(h)$ in which frequency characteristics in the external and middle ears of the subject are considered based on notch width and the upper limit value thereof in the case where the subject can perceive the inspection sound and estimating the filter shape from coefficients p, r obtained above, and an auditory filter display element for displaying the estimated filter shape.

With this apparatus, there is provided the auditory filter calculation element for calculating the coefficient p of the roex (p, r) filter by applying the correction function $W_c(h)$ in which frequency characteristics in the external and middle ears of the subject are considered and for estimating the filter shape from the coefficients p, r obtained above. It is therefore possible to precisely estimate the shape of the auditory filter effective to perform a diagnosis of hearing impairment, to grasp hearing characteristics of the hearing-impaired, to fit a hearing aid, and the like efficiently and accurately.

Further, it is possible to provide a tone level setting element for amplifying or attenuating the tone generated at the tone generation element to a predetermined level.

In this manner, it is possible to more precisely estimate the shape of the auditory filter by providing the tone level setting element for amplifying or attenuating the tone generated at the tone generation element to a predetermined level.

Further, it is possible to provide the upper limit value calculation element for calculating the upper limit value of the notch width suitable for the subject based on the notch width in the case where the subject can perceive the inspection sound.

By providing the upper limit value calculation element for calculating the upper limit value of notch width suitable for the subject based on the notch width in the case where the subject can perceive the inspection sound, it is possible to more precisely estimate the shape of the auditory filter.

Further, when the threshold masking level $N_x$ and/or the minimum notch width $g_{x-a}$ are measured, it is possible to start transmission of the tone at predetermined time intervals after starting the transmission of a masker to the subject.

In this manner, it is possible to easily judge the validity of response by the subject from the timing of transmission of the tone and the timing of response by the subject.

Next, a method for estimating the shape of an auditory filter according to the present invention by finding a coefficient p of a roex (p, r) filter which is used as a model for the shape of the auditory filter comprises the steps of generating a tone S' which subtracts a given value a from a tone S which adds a given value x to the threshold of hearing T of a subject in a frequency f, generating a masker of notch width g and level $N_x$' including in a notch the frequency f in which frequency characteristics of the external and middle ears of the subject are considered, transmitting to the subject an inspection sound which superposes the masker on the tone S', measuring the minimum notch width $g_{x-a}$ of the subject while varying the notch width g, calculating the coefficient p from an upper limit value $g_{max}$ of the notch width g suitable for the subject from the minimum notch width $g_{x-a}$, the minimum notch width $g_{x-a}$, the value x corresponding to a coefficient r and the value a, and estimating the shape of the auditory filter from the coefficient p calculated above and the value x corresponding to the coefficient r.

In this manner, it is possible to precisely estimate the shape of the auditory filter effective to efficiently and accurately perform a diagnosis of hearing impairment, to grasp hearing characteristics of the hearing-impaired, to fit a hearing aid, and the like by generating the masker of the notch width g and the level $N_x$' including in the notch a frequency f in which the frequency characteristics of the external and middle ears of the subject are considered.

It is also possible to estimate the shape of the auditory filter using the given value x as a parameter.

With this method, it is possible to estimate the shape of the auditory filter corresponding to an input signal level and know the relationship between the input signal level and the auditory filter.

Further, it is possible to determine the threshold masking level $N_x$' based on the tone S which adds the given value x to the threshold of hearing T of the subject in a frequency f.

In this manner, it is possible to more precisely estimate the shape of the auditory filter in which the frequency characteristics of the subject's external and middle ears are considered, by determining the threshold masking level $N_x$' based on the tone S which adds the given value x to the threshold of hearing T of the subject in a frequency f.

It is also possible to estimate the upper limit value $g_{max}$ of the notch width g suitable for the subject from the minimum notch width $g_{x-a}$.

According to this method, it is possible to more precisely estimate the shape of the auditory filter in which the frequency characteristics in the subject's external and middle ears are considered, by estimating the upper limit value $g_{max}$ of the notch width g suitable for the subject from the minimum notch width $g_{x-a}$.

Further, in the case of measuring the threshold masking level $N_x$' and/or the minimum notch width $g_{x-a}$, it is possible to start transmission of the tone at predetermined time intervals after starting the transmission of the masker to the subject.

With this method, it is possible to easily judge the validity of response by the subject from the timing of transmission of the tone and the timing of response by the subject.

An apparatus for estimating the shape of an auditory filter according to the present invention by finding a coefficient p of a roex (p, r) filter which is used as a model for the shape of the auditory filter comprises a tone generation element for generating a tone of a predetermined frequency, a noise generation element for generating noise, which is not provided with a notch, in which frequency characteristics of a subject's external and middle ears are considered, a noise level setting element for amplifying or attenuating the noise generated at the noise generation element to a predetermined level, a notch width setting element for providing the noise with a notch including the frequency of the tone, a notched noise superposition element for superposing the notched noise output from the notch width setting element on a tone output from the tone level setting element, an inspection sound transmission element for transmitting to the subject an inspection sound output from the notched noise superposition element, an auditory filter calculation element for calculating the coefficient p of the roex (p, r) filter based on the notch width and the upper limit value thereof in the case where the subject can perceive the inspection sound and estimating the filter shape from the coefficients p, r obtained above, and an auditory filter display element for displaying the filter shape estimated above.

With this apparatus, it is possible to precisely estimate the shape of the auditory filter effective to efficiently and accurately perform a diagnosis of hearing impairment, to grasp hearing characteristics of the hearing-impaired, to fit a hearing aid, and the like by providing the noise generation element for generating the noise in which frequency characteristic of the subject's external and middle ears are considered.

It is also possible to provide the tone level setting element for amplifying or attenuating the tone generated at the tone generation element to a predetermined level.

In this manner, it is possible to more precisely estimate the shape of the auditory filter by providing the tone level setting element for amplifying or attenuating the tone generated at the tone generation element to a predetermined level.

It is also possible to provide an upper limit value calculation element for calculating the upper limit value of notch width suitable for the subject based on the notch width in the case where the subject can perceive the inspection sound.

According to this apparatus, it is possible to more precisely estimate the shape of the auditory filter by providing the upper limit value calculation element for calculating the upper limit value of notch width suitable for the subject based on the notch width in the case where the subject can perceive the inspection sound.

Further, it is possible to start transmission of the tone at predetermined time intervals after starting the transmission of the masker to the subject when the threshold masking level $N_x'$ and/or the minimum notch width $g_{x-a}$ are measured.

In this manner, it is possible to easily judge the validity of response by the subject from the timing of transmission of the tone and the timing of response by the subject.

The above and other objects, features and advantages of the present invention will become more apparent from the following description when taken in conjunction with the accompanying drawings.

DETAILED DESCRIPTION OF THE PREFERRED EMBODIMENTS

The preferred embodiments of the present invention will be described hereunder with reference to the accompanying drawings.

Figure 1:
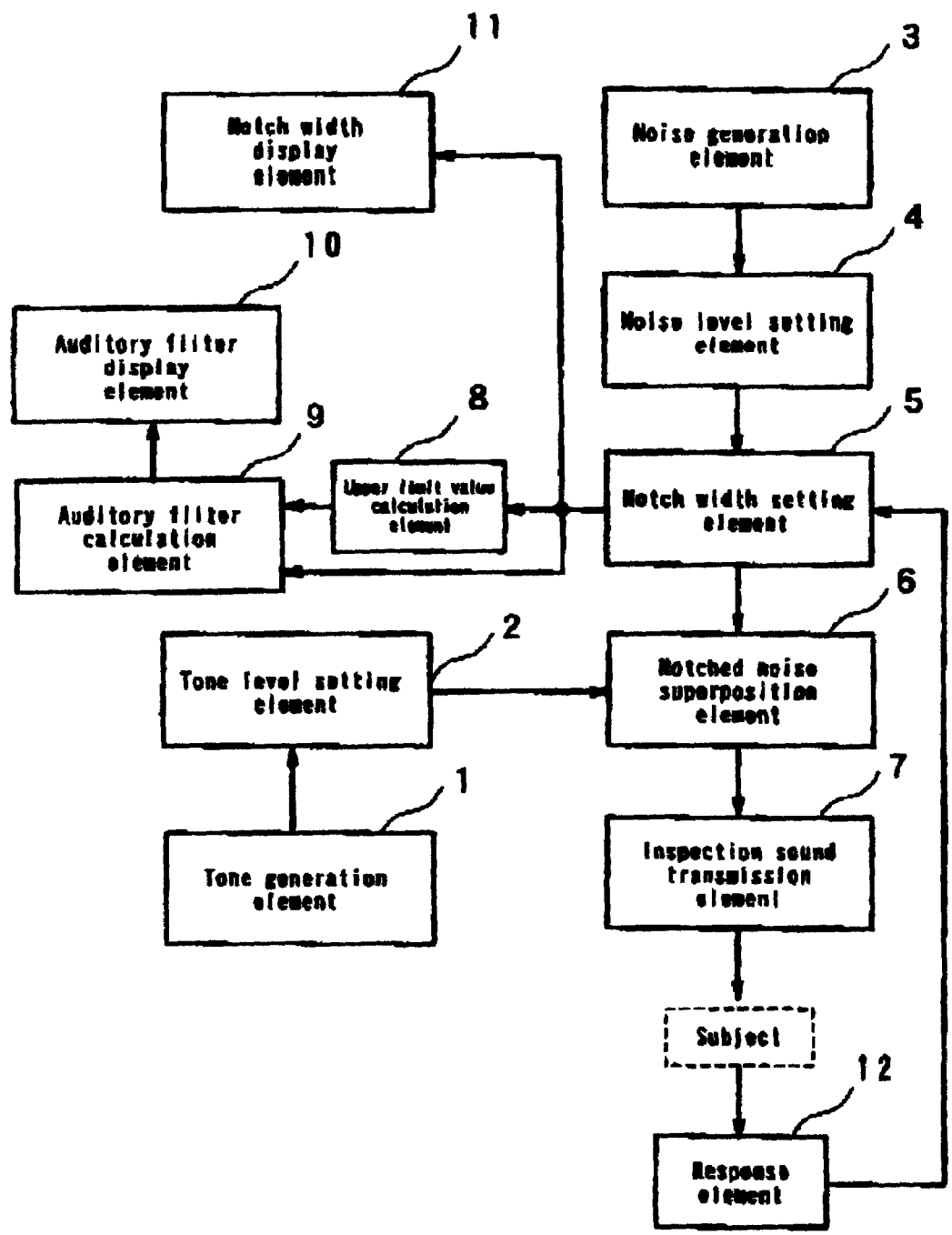
FIG. 1 is a schematic diagram of an apparatus for estimating the shape of an auditory filter according to a first embodiment of the present invention.

As shown in FIG. 1, an apparatus for estimating the shape of an auditory filter according to a first embodiment of the present invention is provided with a tone generation element 1, a tone level setting element 2, a noise generation element 3, a noise level setting element 4, a notch width setting element 5, a notched noise superposition element 6, an inspection sound transmission element 7, an upper limit value calculation element 8, an auditory filter calculation element 9, an auditory filter display element 10, a notch width display element 11, a response element 12, and the like.

The tone generation element 1 outputs a sinusoidal wave signal of a predetermined frequency f as a tone (i.e., a pure tone). A value of the frequency f can be set voluntarily. The tone generation element 1 may be constituted by a CPU to generate the tone by a predetermined program, or constituted by a memory to store a tone signal in advance.

The tone level setting element 2 is designed to amplify or attenuate the tone generated at the tone generation element 1 to a predetermined level. The tone level setting element 2 outputs a tone of the threshold of hearing T [dBSPL] of a certain subject, a tone S of a level T+x [dBSPL] which adds a given value x [dB] to the threshold of hearing T [dBSPL], a tone S' of a level T+x−a [dBSPL] which deducts a given value a [dB] from a level T+x [dBSPL], etc., wherein the relation is x>a.

The noise generation element 3 generates noise which is not provided with a notch or is notchless (white noise etc.). The noise generation element 3 may be constituted by a CPU to generate the noise by a predetermined program, or constituted by a memory to store a noise signal in advance.

The noise level setting element 4 is designed to amplify or attenuate the noise generated at the noise generation element 3 to a predetermined level. The noise level setting element 4 outputs the noise etc. of a level $N_x$ which can mask a tone S of a level T+x[dBSPL].

The notch width setting element 5 provides the noise output from the noise level setting element 4 with a notch of which the center frequency $f_c$ is the same ($f_c$=f) as the frequency f of the tone. Notch width g of this notch is varied at any time by response of the subject. The notch width setting element 5 can be constituted as such a filter that realizes the desired notch, or constituted to store a plurality of notched noises (i.e., a masker) in a memory in advance so that the noise having various notches can be selectively used at any time.

The notched noise superposition element 6 superposes notched noise of the center frequency $f_c$, the notch width g and the level $N_x$ output from the notch width setting element 5 on the tone S' output from the tone level setting element 2 to provide the inspection sound.

The inspection sound transmission element 7 transmits to a subject the inspection sound output from the notched noise superposition element 6. The subject listens to the inspection sound and responds whether he can perceive the tone S'.

The upper limit value calculation element 8 calculates an upper limit value $g_{max}$ of notch width suitable for the subject based on the notch width g in the case where the subject can perceive the inspection sound.

The auditory filter calculation element 9 calculates a filter coefficient p of a roex (p, r) filter based on the notch width g and the upper limit value $g_{max}$ thereof in the case where the subject can perceive the tone S' and estimates the shape of the auditory filter from the filter coefficients p and r obtained above.

The roex (p, r) filter is defined by the following formula (1):

$$w(g)=(1-r)(1+pg)e^{-pg}+r \qquad (1)$$

where p is a coefficient corresponding to a band width (i.e., an angle of slope) of a filter, r is a coefficient corresponding to a dynamic range of the filter, and g is the notch width ($=\Delta f/f_c$), i.e., the value normalizing a distance from the center frequency of the auditory filter. To show the auditory filter as a model using the formula (1), notched noise masking data Ps(g) obtained from the notched noise masking are used. This is defined by the following formula (2):

$$Ps(g) = 2Kf_cN_x \int_g^{g_{max}} w(h)dh \qquad (2)$$

where $g_{max}$ is the upper limit value of the notch width g, K is sensitivity of each person, $f_c$ is the center frequency of the notched noise, and $N_x$ is a level of a masker M.

The audio filter display element 10 displays the shape of the auditory filter from the filter coefficients p and r obtained by the audio filter calculation element 9.

The notch width display element 11 displays the notch width g of the masker output from the notch width setting element 5.

The response element 12 outputs a response signal in the case where it can perceive the tone S' from the inspection sound which is transmitted from the inspection sound transmission element 7 by way of the operation of the subject, and outputs a response signal in the case where it cannot perceive the tone S'. The response signal in the case where the response element 12 cannot perceive the tone S' is output to the notch width setting element 5.

Only the response signal in the case where the subject could perceive the tone S' is used. If the response signal in the case where the subject can perceive the tone S' for the predetermined time is not output, it is considered that the subject can not perceive it and the program can go to the next step.

An operation of the apparatus for estimating the shape of the auditory filter according to the first embodiment of the present invention as constituted above will now be explained hereunder.

The masker M is superposed on the tone S' at the notched noise superposition element 6 to produce the inspection sound. The produced inspection sound is transmitted to the subject from the inspection sound transmission element 7.

The subject listens to the inspection sound and responds through the response element 20 whether he can perceive the tone S'.

Figure 2:
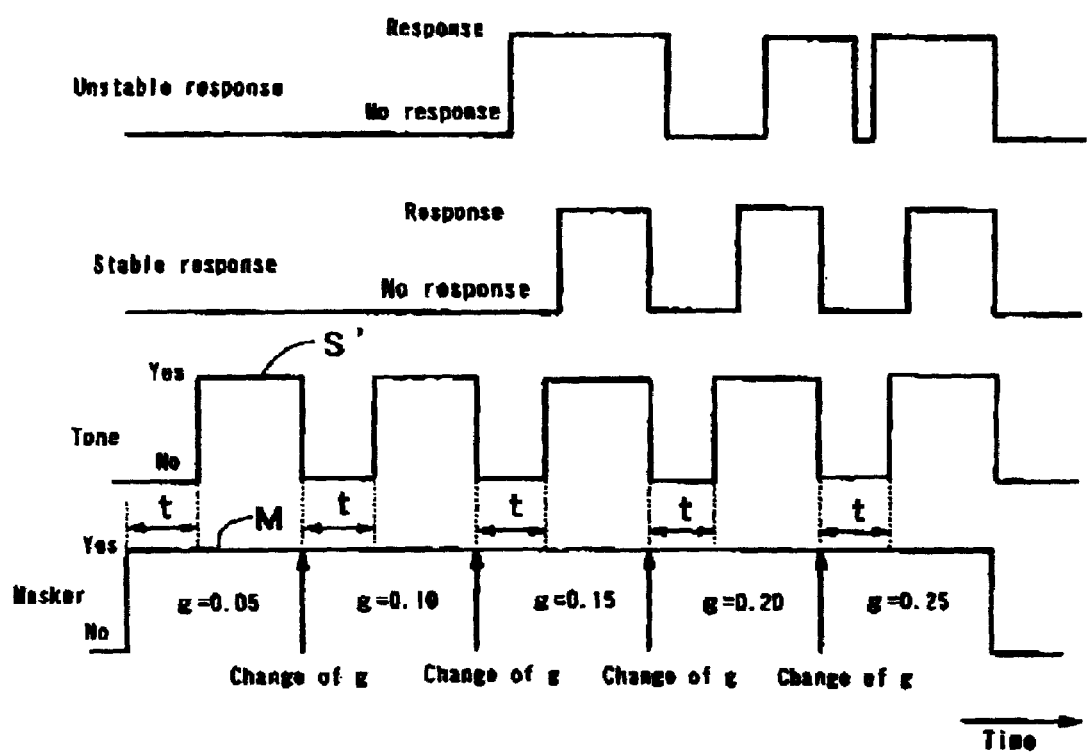
FIG. 2 is a timing chart showing the relationship between transmission of an inspection sound and response by a subject.

As shown in FIG. 2, when the first inspection sound is transmitted to the subject, it is possible to set the level of the tone S' output from the tone level setting element 2 at 0 only for the predetermined time t at the start of transmission of the inspection sound. (In other words, transmission of the tone S' can be delayed only for the predetermined time t relative to the masker M).

In the notch width setting element 5, a new masker M is produced according to the response, and output again to the notched noise superposition element 6. Thus, the notch width g of the masker M can be automatically set according to the response by the subject (it can be constituted by a CPU etc. to prepare the exclusive program), or a measurer can manually instruct the setting each time.

Even when a new inspection sound is transmitted to the subject after increasing the notch width g, it is also possible to set the level of the tone S' output from the tone level setting element 2 at 0 (i.e., the transmission of the tone S' can be delayed only for the predetermined time t relative to the masker M) only for the predetermined time t at the start of transmission of the new inspection sound.

Figure 3:
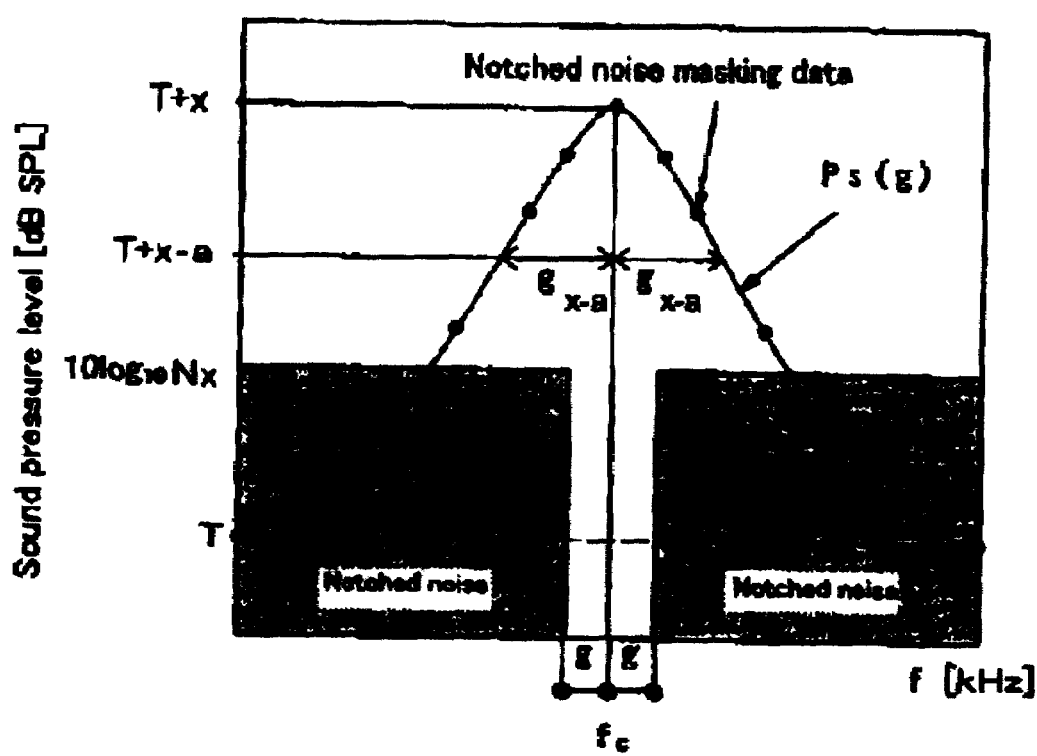
FIG. 3 is an explanatory view of a method for estimating the shape of the auditory filter according to the present invention.

The notch width g during measurement is displayed at the notch width display element 11. By gradually increasing the notch width g, the notch width setting element S measures the minimum notch width (i.e., the threshold notch width) $g_{x-a}$ whereby the tone S' can be perceived by the response of the subject. The minimum notch width $g_{x-a}$ is, as shown in FIG. 3, equivalent to a band width at a point attenuated by a [dB] from the apex in notched noise masking data characteristics.

The upper limit value calculation element 8 calculates the upper limit value $g_{max}$ using the minimum notch width $g_{x-a}$ measured by the notch width setting element 5.

In the auditory filter calculation element 9, a filter coefficient p of a roex (p, r) filter is calculated as shown below using the minimum notch width $g_{x-a}$ measured by the notch width setting element 5 and the upper limit value $g_{max}$ calculated by the upper limit value calculation element 8. By taking the difference between Ps(0) and $Ps(g_{x-a})$ in the formula (2), the following formula (3) is given.

$$10 \log_{10}\{Ps(0)/Ps(g_{x-a})\} = (T+x) - (T+x-a) = a \qquad (3)$$
$$a = 10 \log_{10}[-(1-r)(2+pg_{max})\exp(-pg_{max}) + prg_{max} + 2(1-r)] -$$
$$10 \log_{10}[-(1-r)(2+pg_{max})\exp(-pg_{max}) +$$
$$prg_{max} + (1-r)(2+pg_{x-a})\exp(-pg_{x-a}) - prg_{x-a}]$$

In this formula (3), the value of $g_{x-a}$ is a measured value and r is $10 \log_{10} r = -x$ using a coefficient x which determines the dynamic range. Since a is a constant determined by measuring conditions, if the value of $g_{max}$ is determined, it is possible to calculate the value of a filter coefficient p.

The following is considered as a method for determining the value of $g_{max}$. The value of the notch width g (hereinafter referred to as "$g_t$") where the threshold of signal detection and the threshold of hearing coincide is about $g_t=0.6\sim0.7$ when a masker level is $10 \log_{10} N_x=40$ dBSPL/Hz in a person of a normal hearing, and the integral of an interval of $g_{max}>0.8$ rarely affects the value of notched noise masking data Ps(g).

Accordingly, referring to the past measurement data of the auditory filter, the relationship between the value of $g_{max}$ and the value of $g_t$ can be expressed by the following formula (4):

$$g_{max} = Cg_t \qquad (4)$$

where the value of C is about $1.1\sim1.3$. On the other hand, according to a simplified measurement method of the present invention, since the measured value is only the notch width $g_{x-a}$, the value of the notch width $g_t$ where the threshold of signal detection and the threshold of hearing coincide is unknown. Further, it is known that the value of the notch width $g_t$ where the threshold of signal detection and the threshold of hearing coincide also varies with the dynamic range (corresponding to the value x) from the measurement result (i.e., the relationship between the notch width g and the threshold of signal detection [dBSPL]). Accordingly, it is necessary to estimate the value of $g_{max}$ from the notch width $g_{x-a}$ for the value of x and the relationship between the value of $g_{max}$ and the value of $g_{x-a}$ can be given by the following formula (5):

$$g_{max} = A_x g_{x-a} \qquad (5)$$

where $A_x$ is a constant which varies with the value of x. When the value of $g_{max}$ is calculated using the measurement result (i.e., the value of $g_t$) of two subjects of normal hearing supposing that C is 1.2, the value of this $A_x$ can be experimentally determined from the value of $g_{max}$ and the value of $g_{x-a}$. The value of $A_x$ is shown in the following table 1.

TABLE 1

| xdB | a | $g_t$ | $g_{max} = 1.2\, g_t$ | $g_{x-a}$ | $A_x = g_{max}/g_{x-a}$ |
|---|---|---|---|---|---|
| 10 | 5 | 0.29 | 0.35 | 0.111 | 3.15 |
| 15 | 5 | 0.37 | 0.44 | 0.097 | 4.54 |
| 20 | 10 | 0.46 | 0.55 | 0.146 | 3.77 |
| 30 | 10 | 0.58 | 0.70 | 0.156 | 4.49 |

In Table 1, the value of $A_x$ is calculated by measuring the value of $g_t$ with x=10, 15, 20 or 30 [dB], but it is also possible to prepare the value of $A_x$ in advance with for example x=40 or 50 [dB].

Accordingly, in the auditory filter calculation element 9, the filter coefficient p of the roex (p, r) filter is calculated by entering the upper limit value g max, the minimum notch width $g_{x-a}$, the value corresponding to the coefficient r, and the value a in the formula (3). Further, the shape of the auditory filter is estimated from the filter coefficients p and r.

The auditory filter display element 10 displays the filter shape from the filter coefficient p and the value x corresponding to the filter coefficient r.

Figure 9:
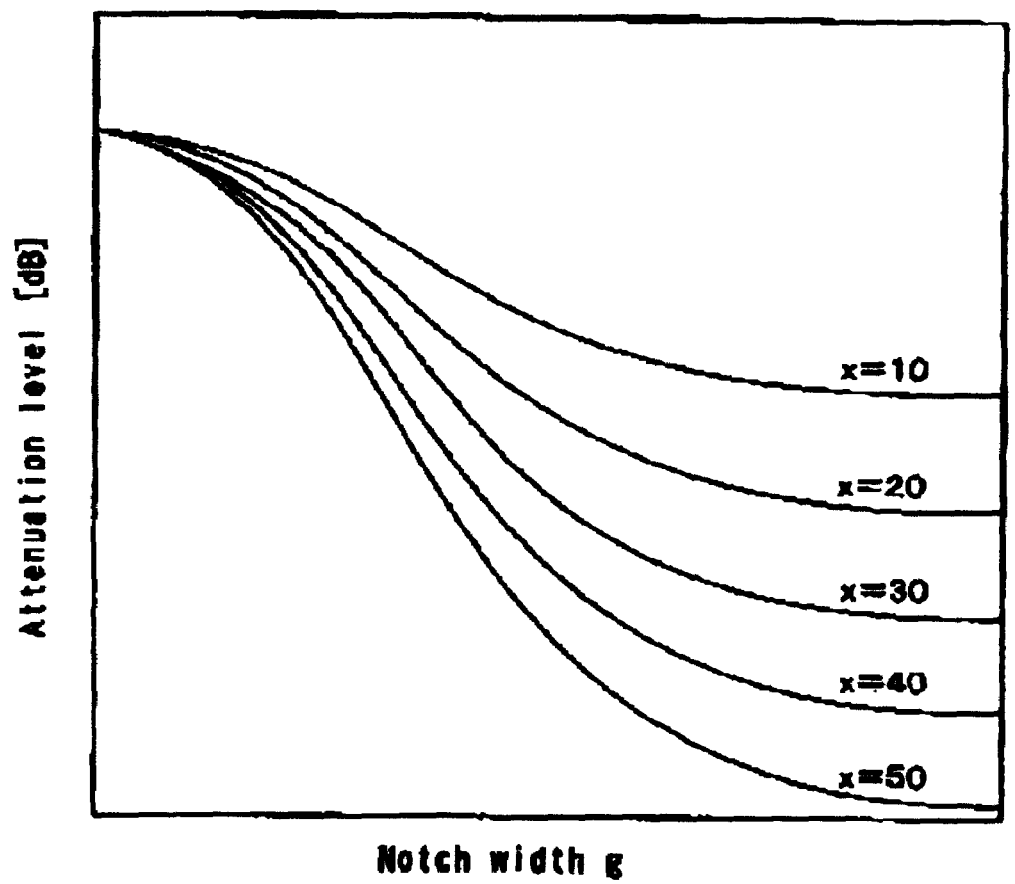
FIG. 9 is a view showing the shape of the auditory filter found in the present invention.

Thus, the estimated value of the filter coefficient p is found respectively by setting the value x corresponding to the filter coefficient r at, for example, 10, 20, 30, 40 or 50 [dB]. As shown in FIG. 9, the shape of the auditory filter (the notch width g in the horizontal axis; an attenuation level [dB] in the vertical axis) is displayed using the value x as a parameter.

Figure 4:
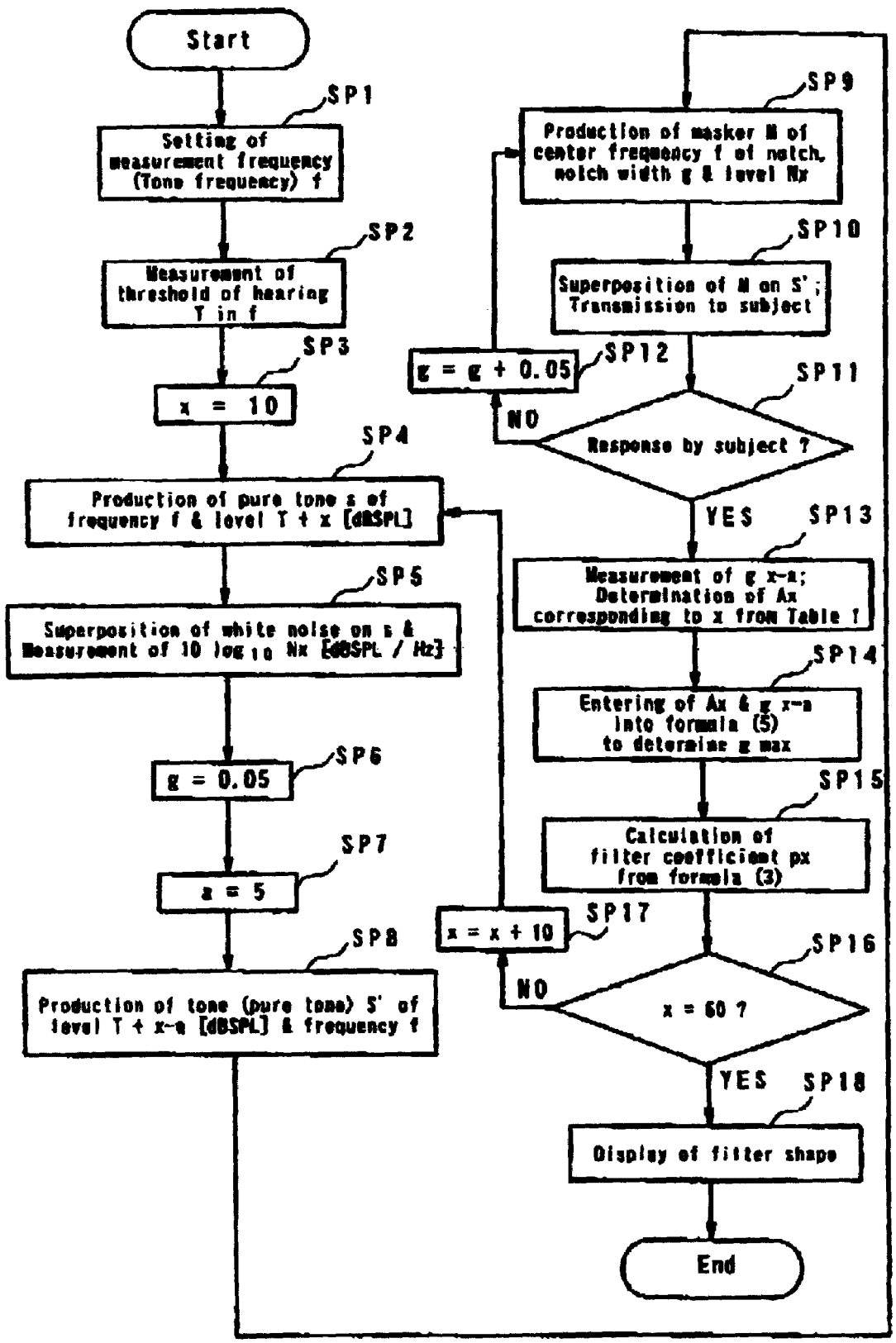
FIG. 4 is a flow chart showing the steps of a method for estimating the shape of the auditory filter according to the first embodiment of the present invention.

Next, a method for estimating the shape of the auditory filter according to the first embodiment of the present invention will now be explained with reference to the flow chart of FIG. 4.

First, in step SP 1, a frequency to be measured (i.e., a tone frequency) f is set and in step SP 2, the pure-tone threshold of hearing T [dBSPL] in the frequency f is measured in a condition where noise is not added.

Then, in step SP 3, a value of a coefficient x is set to determine a dynamic range of the notched noise masking data, wherein x=10. In step SP 4, the pure tone S of the frequency f [Hz] and the level T+x [dBSPL] is produced.

In step SP 5, the white noise of which the level is sufficiently small is superposed on the tone S to measure the minimum level (i.e., the threshold masking level) $10\log_{10} N_x$ [dBSPL/Hz] where the subject cannot perceive the tone S while gradually raising the white noise level.

In step SP 6, the notch width g of noise of the level $10\log_{10} N_x$ [dBSPL/Hz] is set at a predetermined value, wherein g=0.05. In step SP 7, the value a [dB] which is subtracted from the level T+x [dBSPL] of the tone S is set at a predetermined value (x>a), wherein a=5.

In step SP 8, the pure tone S' of the frequency f [Hz] and level T+x−a [dBSPL] is produced. In step SP 9, a masker M of a notch whose center frequency is $f_c(=f)$, notch width g and level $10\log_{10} N_x$ [dBSPL/Hz] is produced.

Then, in step SP 10, the masker M is superposed on the tone S' to transmit it to the subject as an inspection sound. Also, in step SP 11, the subject is asked to judge whether or not he can perceive the tone S' from the inspection sound. If the subject does not make a response that he has perceived the tone S', the program goes to step SP 12 to increase the value of the notch width g (wherein an increment is 0.05). The steps 9 to 11 are repeated until the subject makes a response that he can perceive the tone S'.

As shown in FIG. 2, when the inspection sound is first transmitted to the subject, it is possible to set the level of the tone S' output from the tone level setting element 2 at 0 only for the predetermined time t at the start of transmission of the inspection sound (In other words, transmission of the tone S' can be delayed only for the predetermined time t relative to the masker M). Similarly, when a new inspection sound is transmitted to the subject after increasing the notch width g at step SP 12, it is also possible to set the level of the tone S' output from the tone level setting element 2 at 0 only for the predetermined time t at the start of transmission of the new inspection sound.

When the timing of transmission start of the tone S' is remarkably different from the timing of response, it is possible to repeat the measurement under the same conditions as before until a stable response can be obtained. Also, the predetermined time t need not be a constant value, but can be changed at random for each measurement.

In this manner, if the timing of response by the subject is observed by delaying the transmission of the tone S' only for the predetermined time t relative to the masker M at the time of transmission of the first inspection sound or by suspending the transmission of only the tone S' when the value of the notch width g of the masker M has been varied and transmitting the tone S' to the subject after the predetermined time t has passed, it is considered that the validity of response by the subject can be judged.

As shown in FIG. 2, if there is a response that the subject has perceived the tone S' after it is transmitted to him and there is no such a response at the same time as the stoppage of transmission thereof, it is considered that the response by the subject is normal. On the other hand, if there is a response that the subject has perceived the tone S' before transmission and such a response is maintained even after the stoppage of transmission thereof, it is considered that the response by the subject is abnormal. In this case, it may be necessary to conduct the measurement again or the level of the tone S' and/or the masker M can be changed.

In step SP 11, if there is a response that the subject has perceived the tone S', the method proceeds to the step SP13.

In step SP 13, the notch width g at that time is determined to be the minimum notch width $g_{x-a}$ of the subject. Then, the value of $A_x$ in the set value x (=10 [dB]) is determined using Table 1 ($A_x$=3.15).

In step SP 14, the value of $A_x$ (3.15) and the value of the measured minimum notch width $g_{x-a}$ are entered into the formula (5) to determine the value of the upper limit value $g_{max}$ of the notch width g suitable for the subject.

In step SP 15, the measured minimum notch width $g_{x-a}$, the upper limit value $g_{max}$ of the notch width estimated from this minimum notch width $g_{x-a}$, the value x corresponding to a preset coefficient r, and the value a are entered into the formula (3) to calculate the estimated value of a filter coefficient $p_x$ of a roex (p, r) filter.

Then, in step SP 16, it is judged whether or not x=50 is satisfied. If x=50 is not satisfied, the program goes to step SP 17 to obtain the relationship x=x+10. The steps 4 to 17 are repeated until x=50 is obtained, wherein the estimated value of the filter coefficient $p_x$ is calculated for a new x (x=20, 30, 40 or 50 [dB]) in accordance with the formula (3). An increment of x is 10 herein, and measurements up to x=50 are conducted.

When x=50 is satisfied in step SP 16, the program goes to step SP 18. As shown in FIG. 9, the shape of the auditory filter using the value x as a parameter (x=10, 20, 30, 40, or 50 [dB]) is displayed in step SP 18 (The horizontal axis shows the notch width g and the vertical axis shows an attenuation level).

Figure 10:
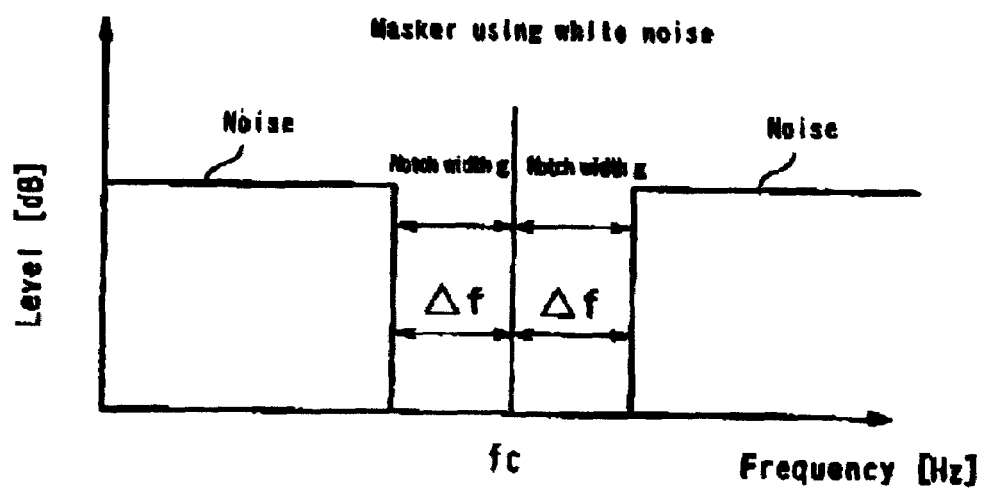
FIGS. 10(a), 10(b) are schematic diagrams of a masker using white noise and a masker using band noise, respectively.
Figure 10:
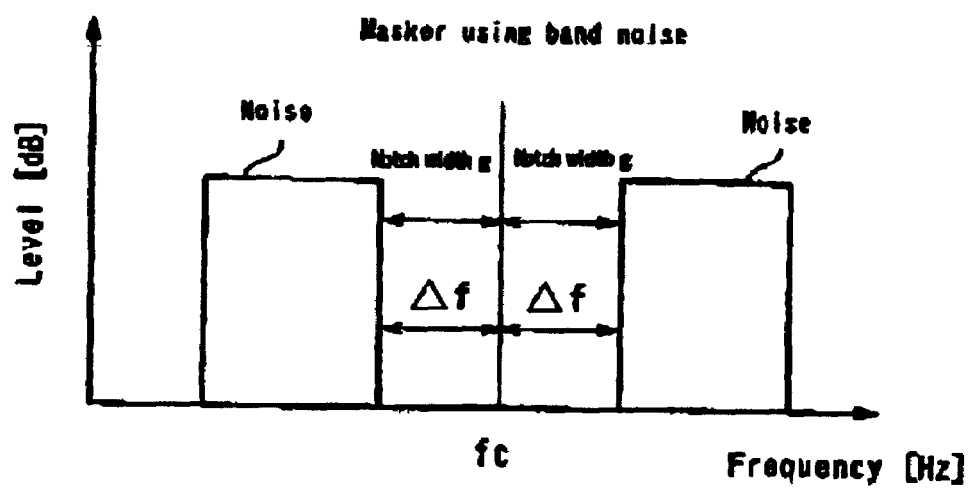

In the first embodiment of the present invention, as shown in FIG. 10 (a), the masker M is produced in such a manner as to add the notch to the white noise. However, the masker M can be constituted by two-band noise (i.e., high frequency side and low frequency side) as shown in FIG. 10 (b).

Figure 5:
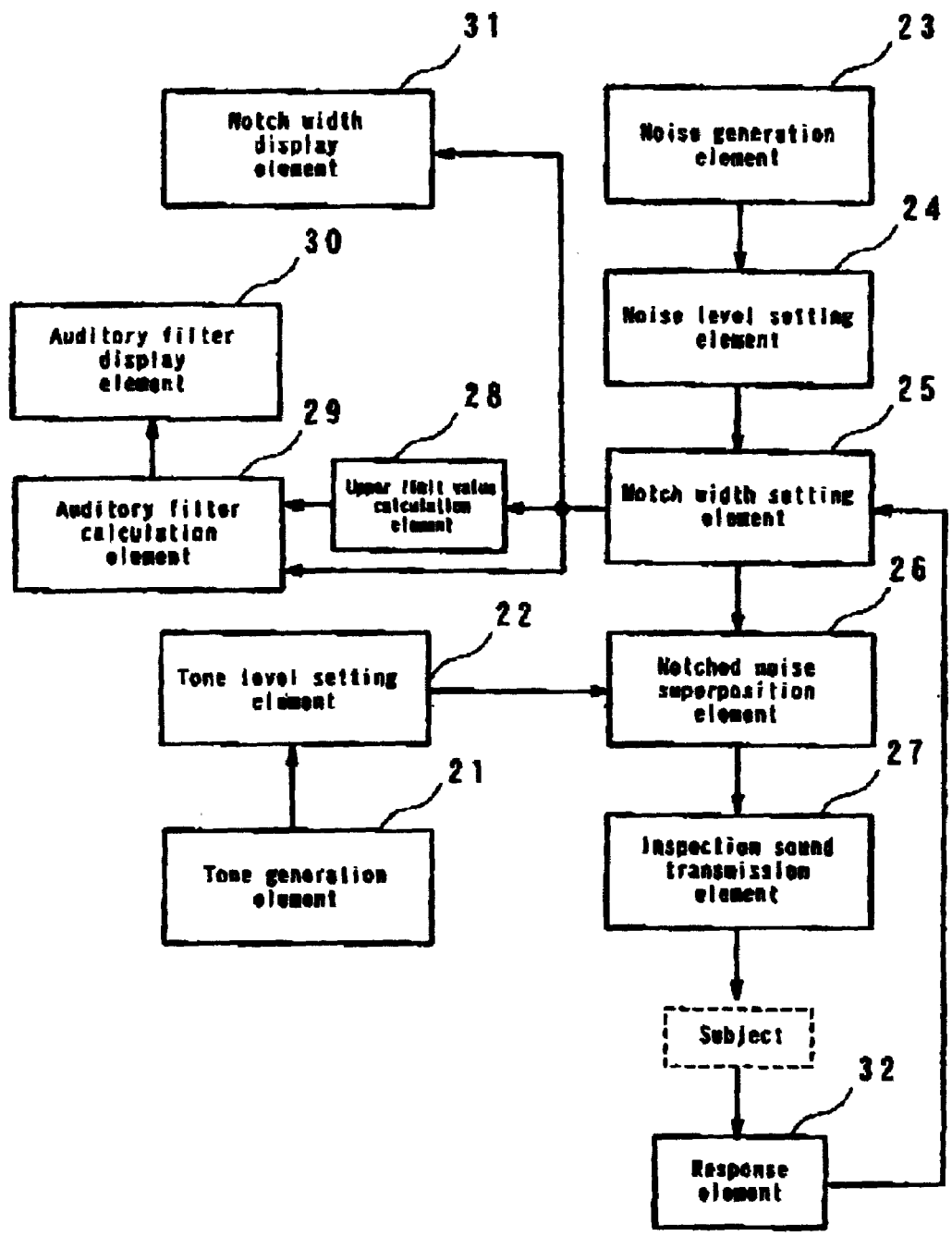
FIG. 5 is a schematic diagram of an apparatus for estimating the shape of an auditory filter according to a second embodiment of the present invention.

Next, an apparatus for estimating the shape of an auditory filter according to a second embodiment of the present invention is provided, as shown in FIG. 5, with a tone generation element 21, a tone level setting element 22, a noise generation element 23, a noise level setting element 24, a notch width setting element 25, a notched noise superposition element 26, an inspection sound transmission element 27, an upper limit value calculation element 28, an audio filter calculation element 29, an audio filter display element 30, a notch width display element 31, a response element 32 and the like.

The tone generation element 21 outputs a sine wave signal of a predetermined frequency f as a tone (i.e., a pure tone). The value of the frequency f can be set voluntarily. The tone generation element 21 can be constituted by a CPU to generate the tone in accordance with a predetermined program, or constituted by a memory to store a tone signal in advance.

The tone level setting element 22 amplifies or attenuates the tone generated at the tone generation element 21 to a predetermined level. The tone level setting element 22 outputs a tone of the threshold of hearing T [dBSPL] of a certain subject, a tone S of level T+x [dBSPL] which adds a given value x [dB] to the threshold of hearing T [dBSPL], a tone S' of level T+x−a [dBSPL] which subtracts a given value a [dB] from level T+x [BSPL], etc., where x>a.

The noise generation element 23 generates noise which is not provided with a notch or is notchless (such as white noise). The noise generation element 23 can be constituted by a CPU to produce the noise in accordance with a predetermined program, or constituted by a memory to store a noise signal in advance.

The noise level setting element 24 amplifies or attenuates the noise generated at the noise generation element 23 to a predetermined level. The noise level setting element 24 outputs the noise of level $N_x$ which can mask the tone S of level T+x [dBSPL], etc.

The notch width setting element 25 provides the noise output from the noise level setting element 24 with a notch of which the center frequency $f_c$ is the same as a frequency f of the tone. The notch width g is varied at any time in accordance with the response of the subject. The notch width setting element 25 can be constituted as such a filter as to realize a desired notch, or a plurality of notched noise (i.e., maskers) can be stored in a memory in advance so that a noise with various kinds of notches can be selectively used at any time.

The notched noise superposition element 26 superposes the notched noise of the center frequency $f_c$, the notch width g and level $N_x$ output from the notch width setting element 25 on the tone S' output from the tone level setting element 22 to produce an inspection sound.

The inspection sound transmission element 27 transmits to the subject the inspection sound output from the notched noise superposition element 26. The subject listens to the inspection sound and responds whether or not he can perceive the tone S'.

The upper limit value calculation element 28 calculates the upper limit value $g_{max}$ of the notch width suitable for the subject based on the notch width g in the case where the subject can perceive the inspection sound.

The auditory filter calculation element 29 calculates a filter coefficient p of a roex (p, r) filter based on the notch width g and the upper limit value $g_{max}$ in the case where the subject can perceive the inspection sound S' and estimates the shape of the auditory filter from the filter coefficients p and r obtained above.

The roex (p, r) filter can be defined by the following formula (7):

$$w(g)=(1-r)(1+pg)e^{-pg}+r \qquad (7)$$

where p is a coefficient corresponding to the band width (i.e., an angle of slope) of a filter, r is a coefficient corresponding to a dynamic range of the filter, and g is a notch width ($=\Delta f/f_c$) which is a value which normalizes the distance from the center frequency of the auditory filter. Notched noise masking data Ps(g) obtained by notched noise masking is used to model the auditory filter in the formula (1). This is defined by the following formula (8):

$$Ps(g) = 2Kf_c N_x \int_g^{g_{max}} w(h)dh \qquad (8)$$

where $g_{max}$ is the upper limit value of the notch width g, K is the sensitivity of each person, $f_c$ is the center frequency of the notched noise, and $N_x$ is a level of the masker M.

The auditory filter display element 30 displays the shape of an auditory filter from the filter coefficients p and r obtained by the auditory filter calculation element 29.

The notch width display element 31 displays the notch width g of the masker output from the notch width setting element 25.

The response element 32 outputs a response signal in the case where the subject can perceive the tone S' from the inspection sound which is transmitted from the inspection sound transmission element 27 by way of the operation of the subject, and a response signal in the case where the subject cannot perceive the tone S'. The response signal in the case where the response element 32 cannot perceive the tone S' is output to the notch width setting element 25.

It is also possible to use only the response signal in the case where the subject can perceive the tone S'. If the response signal in the case where the subject can perceive it for a predetermined time is not output, it is considered as if he could not perceive the tone S' and the program can go to the next step.

An operation of the apparatus for estimating the shape of the auditory filter according to the second embodiment of the present invention as constituted above will now be explained hereunder.

The masker M is superposed on the tone S' in the notched noise superposition element 26 to produce the inspection sound. The produced inspection sound is transmitted from the inspection sound transmission element 27 to the subject.

The subject listens to the inspection sound and responds via the response element 32 whether or not he can perceive the tone S'.

As shown in FIG. 2, when the first inspection sound is transmitted to the subject, it is possible to set the level of the tone S' output from the tone level setting element 2 at 0 only for a predetermined time t at the start of transmission of the inspection sound. (In other words, it is possible to delay the transmission of the tone S' only for a predetermined time relative to the masker M).

In the notch width setting element 25, a new masker M is produced in accordance with the response and output again to the notched noise superposition element 26. Setting of the notch width g of the masker M can be automatically effected in accordance with the response of the subject (e.g. it can be constituted by a CPU etc. to prepare an exclusive program) or a measurer can manually instruct the setting.

Further, when a new inspection sound is transmitted to the subject after increasing the notch width g, it is also possible to set the level of the tone S' output from the tone level setting element 22 to 0 only for a predetermined time at the start of transmission of the new inspection sound. (In other words, it is possible to delay the transmission of the tone S' only for a predetermined time t relative to the masker M).

The notch width g during measurement is displayed at the notch width display element 31. The notch width setting element 25 measures the minimum notch width (i.e., the threshold notch width) where the tone S' can be perceived by the response of the subject is measured by gradually increasing the notch width g. The minimum notch width $g_{x-a}$ is, as shown in FIG. 3, equivalent to the band width of a point attenuated by a [dB] from the apex in the notched noise masking data characteristics.

The upper limit value calculation element 28 calculates an upper limit value $g_{max}$ using the minimum notch width $g_{x-a}$ measured by the notch width setting element 25.

In the auditory filter calculation element 29, a filter coefficient p of a roex (p, r) filter is calculated as follows using the minimum notch width $g_{x-a}$ measured by the notch width setting element 25 and the upper limit value $g_{max}$ calculated by the upper limit value calculation element 28. A difference a between Ps(0) and Ps($g_{x-a}$) in the formula (8) is expressed in the following formula (9).

$$10 \log_{10}\{Ps(0)/Ps(g_{x-a})\}=(T+x)-(T+x-a)=a \quad (9)$$

The difference a is expressed in the following formula (10) from the formulas (8) and (9):

$$a = 10 \log_{10}[-(1-r)(2+pg_{max})\exp(-pg_{max})+prg_{max}+2 \\ (1-r)]-10 \log_{10}[-(1-r)(2+pg_{max})\exp(-pg_{max})+ \\ prg_{max}+(1-r)(2pg_{x-a})\exp(-pg_{x-a})-prg_{x-a}] \quad (10)$$

where the value of $g_{x-a}$ is the measured value, r is $10 \log_{10} r=-x$ using a coefficient x for determining a dynamic range, and a is a given constant to be determined by measurement conditions. Accordingly, if the value of $g_{max}$ is determined, the value of the filter coefficient p can be calculated from the formula (10).

Now, the level of masker M used in measurement is produced on condition that a sound pressure level per 1 Hz is uniform or the same. However, when coming through the external ear and the middle ear, the masker M is affected by the frequency characteristics of the external and middle ears of the subject. As a result, the frequency characteristics of the masker in the case where it reaches the middle ear are not always uniform or the same.

Accordingly, the formula (8) becomes the following formula (11) as a result of taking the frequency characteristics of the external and middle ears of the subject into consideration:

$$Ps(g) = 2Kf_c N_x \int_g^{g_{max}} w_c(h)w(h)dh \quad (11)$$

where $w_c(h)$ is a correction function for enabling the sound pressure level per 1 Hz to have uniform or the same frequency characteristics irrespective of the frequency characteristics of the external and middle ears of the subject even when the masker M of which the sound pressure level per 1 Hz is uniform or the same has reached the internal ear via the external and middle ears.

It is not necessary to individually change the correction function $w_c(h)$ because differences among individuals of the frequency characteristics in the eternal and middle ears of the persons of normal hearing are small.

The correction function $w_c(h)$ of the person of normal hearing can be determined using MAP (minimum audible pressure), MAF (minimum audible field), and ELC (equal loudness contour).

There are two methods for measuring the absolute threshold of a sound. The absolute threshold of sound means the minimum level of the sound that can be detected in a condition where there is no disturbing or interfering sound. One is a method for measuring the relationship between the frequency and the minimum audible pressure near the entrance of an external auditory meatus or inside thereof and the measured threshold is called the minimum audible pressure "MAP". The other is a method for measuring the level of a sound which is transmitted from a speaker in a large anechoic or free-field room at the central position of a listener's head and the measured threshold is called minimum audible field "MAF".

Further, there is a method whereby a pure tone and an inspection sound of 1000 Hz of which the level of sound has been secured are alternately transmitted and the intensity of the inspection sound is caused to change to allow its loudness to coincide with the pure tone. This method is performed relative to the pure tone with various frequencies and as a result, the equal loudness contour "ELC" concerning the loudness of sound is obtained.

On the other hand, there are cases where the hearing-impaired have trouble in their external and/or middle ears. Since it is estimated that the frequency characteristics of their external and middle ears are different from those of people with normal hearing, it is necessary to determine a correction function $w_c(h)$ in which the frequency characteristics of the external and/or middle ears of each of the hearing-impaired are considered.

Upon determination of the correction function $w_c(h)$, since the hearing-impaired having trouble in their external and/or middle ears have different values of audiogram of bone and air conduction from those of people of normal hearing, it is possible to consider the correction by means of using these differences. It is also possible to determine the frequency characteristics of the external ear from these frequency characteristics near the entrance of the external auditory meatus and a result of measuring these frequency characteristics by providing a probe microphone near the eardrum.

When the value of the filter coefficient p is calculated from the minimum notch width $g_{x-a}$ using the formula (10), if the correction function $w_c(h)$ is applied thereto, the formula (10) becomes the following formula (12) from the formula (11).

$$a = 10 \log_{10}\{Ps(0)/Ps(g_{x-a})\} = 10 \log_{10}\left[\frac{\int_g^{g_{max}} w_c(h)w(h)dh}{\int_{g_{x-a}}^{g_{max}} w_c(h)w(h)dh}\right] \quad (12)$$

The following method is considered to determine the value of $g_{max}$. The value of notch width g (hereinafter referred to as "$g_t$") whereby the threshold of signal detection and the threshold of hearing coincide is about $g_t$=0.6~0.7 in the case where the masker level is 10 $\log_{10} N_x$=40 dBSPL/Hz in the people of normal hearing. Accordingly, the integral of an interval of $g_{max}$>0.8 rarely affects the value of notched noise masking data Ps(g).

Accordingly, referring to the past measurement data of the auditory filter, the relationship between the value of $g_{max}$ and the value of $g_t$ can be defined by the following formula (13):

$$g_{max} = Cg_t \quad (13)$$

where the value of C is about 1.1~1.3. On the other hand, in the simplified measuring method of the present invention, since the measured value is only the notch width $g_{x-a}$, the value of notch width $g_t$ whereby the threshold of signal detection and the threshold of hearing coincide is unknown. In addition to the above, it is known that the value of the notch width $g_t$ whereby the threshold of signal detection and the threshold of hearing coincide also varies with the dynamic range (corresponding to the value x) from the measurement result (i.e., the relationship between the notch width g and the threshold of signal detection [dBSPL]). Accordingly, it is necessary to estimate the value of $g_{max}$ from the notch width $g_{x-a}$ for each value of x and the relationship between the value of $g_{max}$ and the value of $g_{x-a}$ becomes the following formula (14):

$$g_{max} = A_x g_{x-a} \quad (14)$$

where $A_x$ is a constant which varies in accordance with the value of x. The value of $g_{max}$ is first calculated using the measurement result (i.e., the value of $g_t$) for two subjects of normal hearing provided that C=1.2. Then, the value of $A_x$ is experimentally determined from the value of $g_{max}$ and the value of $g_{x-a}$ and shown in the following Table 2.

TABLE 2

| xdB | a | $g_t$ | $g_{max}$ = 1.2 $g_t$ | $g_{x-a}$ | $A_x = g_{max}/g_{x-a}$ |
|---|---|---|---|---|---|
| 10 | 5 | 0.29 | 0.35 | 0.111 | 3.15 |
| 15 | 5 | 0.37 | 0.44 | 0.097 | 4.54 |
| 20 | 10 | 0.46 | 0.55 | 0.146 | 3.77 |
| 30 | 10 | 0.58 | 0.70 | 0.156 | 4.49 |

In Table 2, the value of $g_t$ in x=10, 15, 20, and 30 [dB] is measured to calculate the value of $A_x$, but it is also possible to prepare the value of $A_x$ in for example x=40 and 50 [dB] in advance.

Accordingly, in the auditory filter calculation element 29, the upper limit value $g_{max}$, the minimum notch width $g_{x-a}$, the value x corresponding to a coefficient r, and the value a are entered in the formula (12) to calculate the filter coefficient p of a roex (p, r) filter. Then, the shape of the auditory filter is estimated from the filter coefficients p and r.

Then, in the auditory filter display element 30, the filter shape is displayed from the filter coefficient p and the value corresponding to the filter coefficient r.

In this manner, the value x corresponding to the filter coefficient r is set, for example, at 10, 20, 30, 40, or 50 [dB] to find the estimated value of the filter coefficient p for each value. As shown in FIG. 9, the shape of the auditory filter is displayed therein using the value x as a parameter (The horizontal axis: the notch width g; the vertical axis: the attenuation level [dB]).

Figure 6:
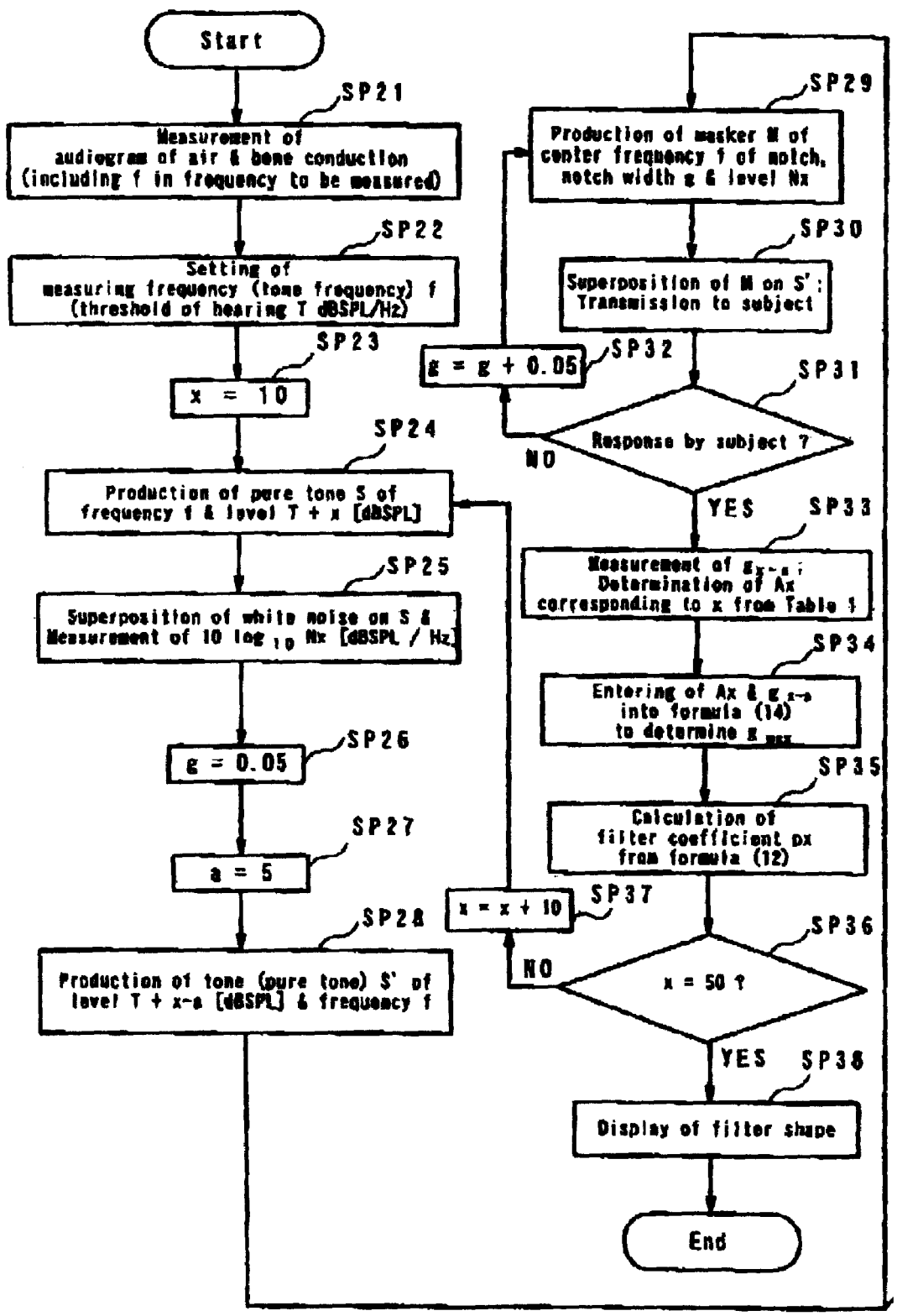
FIG. 6 is a flow chart showing the steps of a method for estimating the shape of the auditory filter according to the second embodiment of the present invention.

A method for estimating the shape of an auditory filter according to the second embodiment of the present invention will now be explained in accordance with the flow chart shown in FIG. 6.

First, in step SP 21, the audiogram of the air conduction and bone conduction including a frequency f is measured in a condition where noise is not added. The threshold of hearing of a pure tone in the frequency f is set at T [dBSPL/Hz]. In step SP 22, the frequency to be measured (i.e., tone frequency) f is set.

In step SP 23, the value of the coefficient x for determining the dynamic range of the notched noise masking data is set. Here x=10. In step SP 24, the pure tone S of frequency f [Hz] and level T+x [dBSPL] is produced.

In SP 25, white noise of which the level is sufficiently low is superposed on the tone S. The minimum level (i.e., the threshold masking level) 10 $\log_{10} N_x$ [dBSPL/Hz] in which a subject cannot perceive the tone S is measured while increasing the level of white noise.

In step SP 26, the notch width g of noise of level 10 $\log_{10} N_x$ [dBSPL/Hz] is set at a predetermined value. Here g=0.05. In step SP 27, the value a [dB] which is subtracted from level T+x [dBSPL] of the tone S is set at a predetermined value (x>a). Here a=5.

Next, in step SP 28, a pure tone S' of a frequency f [Hz] and level T+x−a [dBSPL] is produced. In step SP 29, a masker M of the center frequency of a notch $f_c$(=f), notch width g, and level 10 $\log_{10} N_x$ [dBSPL/HZ] is produced.

In step SP 30, the masker M is superposed on the tone S' to transmit it to a subject as an inspection sound. In step SP 31, the subject is asked to judge whether or not he can perceive the tone S' from the inspection sound. If there is no response indicating that that he can perceive the tone S', step SP 32 is taken, wherein steps 29 to 31 are repeated while increasing the value of the notch width g until there is a response indicating that he can perceive the tone S'.

Now, as shown in FIG. 2, when the inspection sound is first transmitted to the subject, it is possible to set the level of the tone S' output from the tone level setting element 22 at 0 only for a predetermined time t at the start of transmission of the inspection sound. (In other words, it is possible to delay the transmission of the tone S' only for the predetermined time t relative to the masker M). Similarly, after increasing the notch width g in step SP 32, when a new inspection sound is transmitted to the subject, it is also possible to set the level of the tone S' output from the tone level setting element 22 at 0 only for a predetermined time t at the start of transmission of the new inspection sound.

If the timing of start of transmission of the tone S' is remarkably different from the timing of the response, measurement is carried out again in the same conditions as before and this can be repeated until a stable response can be obtained. It is to be noted that the predetermined time t needs not be a fixed value, but can be changed at random for each measurement. In this manner, by delaying the transmission of the tone S' only for the predetermined time t relative to the masker M at the transmission of the first inspection sound, or by stopping once the transmission of only the tone S' when the value of notch width g of the masker M is varied and transmitting the tone S' to the subject after the predetermined time t has passed, if the timing of response by the subject at that time is observed, it is also possible to judge the validity of the response by the subject.

As shown in FIG. 2, if there is a response that the subject has perceived the tone S' after it is transmitted to him and if there is no response that he has perceived the tone S' at the same time when the transmission of the tone S' is stopped, it is considered that the validity of response by the subject is normal. On the other hand, if there is a response indicating that the subject has perceived the tone S' before it is transmitted to him and the response that he has perceived the tone S' is maintained even after stopping the transmission thereof, it is considered that his response is not normal. In this case, problems can be solved by performing the measurement again or by changing the setting of the level of the tone S' and the level of the masker M.

In step SP 31, if there is a response indicating that the subject can perceive the tone S', step SP 33 is taken.

In step SP 33, the notch width g at that time is set as the minimum notch width $g_{x-a}$ of the subject. The value of $A_x$ in the set value x (=10 [dB]) is determined using Table 1 ($A_x$=3.15).

Next, in step SP 34, the value of $A_x$ (3.15) and the value of the measured minimum notch width $g_{x-a}$ are entered in the formula (14) to determine the value of the upper limit value $g_{max}$ of the notch width g suitable for the subject.

In step SP 35, the correction function $w_c(h)$ in the case where MAP, MAF, ELC and the like have been considered and in the case where the difference in the audiogram for the air and bone conduction measured in step SP 21 has been considered, the measured minimum notch width $g_{x-a}$, the upper limit value $g_{max}$ of the notch width estimated from the minimum notch width $g_{x-a}$, the value x corresponding to a preset coefficient r, and the value a are entered into the formula (12) to calculate the estimated value of the filter coefficient $p_x$ (x=10) of the roex (p, r) filter.

Next, in step SP 36, a judgment is made as to whether or not x=50 is satisfied. If x=50 is not satisfied, step SP 37 is taken to have x=x+10, wherein steps 24~37 are repeated to satisfy x=50. An estimated value of the filter coefficient $p_x$ for a new x (x=20, 30, 40, and 50 [dB]) is calculated from the formula (12). Here, an increment width of x is 10 and measurements up to x=50 are conducted.

In step SP 36, if x=50 is satisfied, step SP 38 is taken, wherein as shown in FIG. 9, the shape of the auditory filter is displayed using the value x as a parameter (x=10, 20, 30, 40, and 50 [dB]) (the horizontal axis: notch width g; the vertical axis: attenuation level [dB]).

In the second embodiment of the present invention, as shown in FIG. 10 (a), the masker M is produced in such a manner as to add a notch to the white noise. However, the masker M can be constituted, as shown in FIG. 10 (b), by two-band noise (of the high frequency side and the low frequency side).

Figure 7:
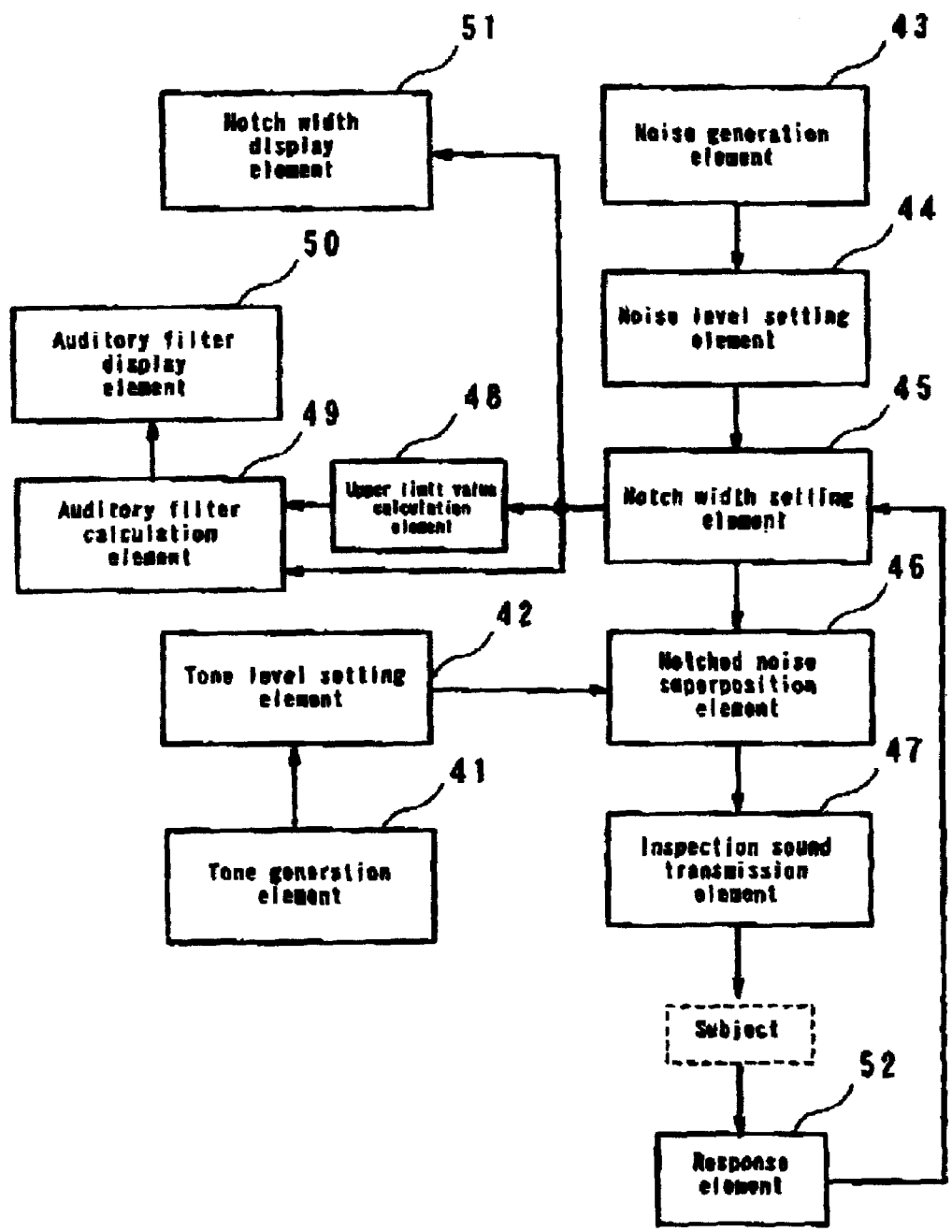
FIG. 7 is a schematic diagram of an apparatus for estimating the shape of an auditory filter according to a third embodiment of the present invention.

An apparatus for estimating the shape of an auditory filter according to a third embodiment of the present invention is provided, as shown in FIG. 7, with a tone generation element 41, a tone level setting element 42, a noise generation element 43, a noise level setting element 44, a notch width setting element 45, a notched noise superposition element 46, an inspection sound transmission element 47, an upper limit value calculation element 48, an auditory filter calculation element 49, an auditory filter display element 50, a notch width display element 51, a response element 52, and the like.

The tone generation element 41 outputs a sine wave signal of a predetermined frequency f as a tone (i.e., a pure tone). The value of the frequency f can be set voluntarily. The tone generation element 41 can be constituted by a CPU to produce the tone in accordance with a predetermined program, or constituted by a memory to store a tone signal therein in advance.

The tone level setting element 42 amplifies or attenuates the tone generated at the tone generation element 41 to a predetermined level. The tone level setting element 42 outputs a tone of the threshold of hearing T [dBSPL] of a certain subject, a tone S of level T+x [dBSPL] which adds a given value x [dB] to the threshold of hearing T [dBSPL], a tone S' of level T+x−a [dBSPL] which takes a given value a from level T+x [dBSPL], and the like, wherein x>a.

The noise generation element 43 generates noise which is not provided with a notch in which frequency characteristics of each subject's external and middle ears have been considered so that a sound pressure level per 1 Hz can be uniform when the noise has reached the internal ear. In this case, it is sufficient to generate uniform exciting noise (UEN) which becomes such a masker as to correct, for example, the frequency characteristics of the external and middle ears of the subject. The noise generation element 43 can be constituted by a CPU to produce the noise in accordance with a predetermined program, or constituted by a memory to store noise signal therein in advance.

In the case of people of normal hearing, since differences among individuals in the external and middle ears are small, it is not necessary to change the correction value individually.

In the case of correction in people of normal hearing, it is possible to determine the correction value using the minimum audible pressure (MAP), the minimum audible field (MAF), and the equal loudness contour (ELC) to produce the masker.

There are two methods for measuring the absolute threshold of a sound which is the minimum level of sound that can be detected in a condition where there is no disturbing sound. One is the method for measuring the relationship between the frequency and the minimum audible pressure near the entrance of the external auditory meatus or inside thereof. The measured threshold is called the minimum audible pressure (MAP). The other is the method for measuring the level of sound transmitted from a speaker in a large free-field or anechoic room (i.e., a room surrounded by sound absorbing high wall) at the central position of a listener's head. The measured threshold is called the minimum audible field (MAF).

There is also a method for alternately transmitting the pure tone and the inspection sound of 1000 Hz of which the level of sound has been fixed and changing the intensity of inspection sound to allow its loudness to coincide with the pure tone. This is performed for the pure tone with various frequencies and as a result, an equal loudness contour of the loudness of sound is obtained. This is called the equal loudness contour (ELC).

On the other hand, there are cases where the hearing-impaired have trouble in their external and/or middle ears. Since it is estimated that the frequency characteristics of their external and middle ears differ from those of people of normal hearing, it is necessary to perform in the case of the hearing-impaired a correction in which the frequency characteristics of each external or middle ear have been considered so as to produce the masker.

In the case of the hearing-impaired who have trouble in their external and/or middle ears, since the values of the audiogram for the bone conduction and the air conduction are different, it is possible to consider the correction using this difference to produce the masker. In the frequency characteristics of the external ear, it is also possible to determine the correction from the frequency characteristics near the entrance of the external auditory meatus and the result of measuring the frequency characteristics by providing a probe microphone near the ear drum.

The noise level setting element 44 amplifies or attenuates the noise generated at the noise generation element 43 to a predetermined level. The noise level setting element 44 outputs the noise of level $N_x'$ which can mask the tone S' of level T+x [dBSPL], etc.

The notch width setting element 45 provides the noise output from the noise level setting element 44 with a notch of which the center frequency $f_c$ is the same ($f_c$=f) as the frequency f of the tone. The notch width g of this notch can be varied at any time in accordance with the response by the subject. The notch width setting element 45 can be constituted as such a filter as to realize a desired notch, or a plurality of notched noises (masker) is stored in a memory in advance so that the noise with various notches can be selectively used at any time.

The notched noise superposition element 46 superposes the notched noise of which the center frequency $f_c$, the notch width g, and the level $N_x'$ output from the notch width setting element on the tone S' output from the tone level setting element to produce an inspection sound.

The inspection sound transmission element 47 transmits to the subject the inspection sound output from the notched noise superposition element 46. The subject listens to the inspection sound and responds whether or not he can perceive the tone S'.

The upper limit value calculation element 48 calculates an upper limit value $g_{max}$ of which the notch width is suitable for the subject based on the notch width g in the case where the subject can perceive the inspection sound.

The auditory filter calculation element 49 calculates a filter coefficient p of a roex (p, r) filter based on the notch width g and the upper limit value $g_{max}$ in the case where the subject can perceive the tone S' and then estimates the shape of the auditory filter from the filter coefficients p and r obtained above.

The roex (p, r) filter is defined by the following formula (15):

$$w(g)=(1-r)(1+pg)e^{-pg}+r \tag{15}$$

where p is a coefficient for showing a band width (i.e., an angle of slope), r is a coefficient for showing the dynamic range of the filter, and g is a notch width (=$\Delta f/f_c$), that is the value whereby the distance from the center frequency of the auditory filter is normalized. Notched noise masking data Ps(g) obtained by notched noise making is used to model the auditory filter by the formula (15). This is defined by the following formula (16):

$$Ps(g) = 2Kf_c N_x \int_g^{g_{max}} w(h) dh \tag{16}$$

where $g_{max}$ is the upper limit value of the notch width g, K is the sensitivity of each individual, $f_c$ is the center frequency of notched noise, and $N_x$ is the level of the masker M when reaching the internal ear.

The auditory filter display element 50 displays the shape of the auditory filter from the filter coefficients p, r obtained by the auditory filter calculation element 49.

The notch with display element 51 displays the notch width g of the masker output from the notch width setting element 45.

The response element 52 outputs a response signal in the case where it perceives the tone S' from the inspection sound which is transmitted from the inspection sound transmission element 47 by way of the operation of the subject, and a response signal in the case where it does not perceive the tone S'. The response signal in the case where the subject cannot not perceive the tone S' is output to the notch width setting element 45.

Only the response signal in the case where the response element 52 perceives the tone S' is used. If the response signal in the case where it perceives the tone S' for a predetermined time is not output, it is considered that the tone S' could not be perceived and the program can go to a next step.

An operation of the apparatus for estimating the shape of the auditory filter according to the third embodiment of the present invention will now be explained.

A masker M in which the frequency characteristics of each subject's external and middle ears have been considered so that a sound pressure level per 1 Hz can be uniform when the tone S' has reached the internal ear is superposed on the tone S' in the notched noise superposition element 46 to produce an inspection sound. The produced inspection sound is transmitted to the subject from the inspection sound transmission element 47.

The subject listens to the inspection sound and responds via the response element 52 as to whether or not he could perceive the tone S'.

Now, as shown in FIG. 2, when the first inspection sound is transmitted to the subject, it is possible to set the level of the tone S' output from the tone level setting element 42 at 0 only for a predetermined time t at the start of transmission of the inspection sound. (In other words, it is possible to delay the transmission of the tone S' only for a predetermined time t after the masker M).

The notch width setting element 45 produces a new masker M in accordance with the response and outputs it again to the notched noise superposition element 46. Here, the setting of the notch width g of the masker M can be automatically effected in accordance with the response from the subject (e.g., setting can be constituted by a CPU etc. to prepare an exclusive program), or a measurer can manually instructs the setting each time.

Even in the case where the new inspection sound is transmitted to the subject after increasing the notch width g, it is also possible to set the level of the tone S' output from the tone level setting element 42 at 0 only for a predetermined time t at the start of transmission of the new inspection sound. (In other words, it is possible to delay the transmission of the tone S' only for a predetermined time t after the masker M).

The notch width g under measurement is displayed at the notch width display element 51. The notch width setting element 45 gradually increases the notch width g and measures the minimum notch width (i.e., the threshold notch width) $g_{x-a}$ whereby the tone S' can be perceived from the response of the subject. The minimum notch width $g_{x-a}$ is, as shown in FIG. 3, equivalent to a band width at a point where attenuated by a [dB] from the apex in the notched noise masking data characteristics. In the masker in FIG. 3, the sound pressure level per 1 Hz is uniform, but in practice it becomes the level in which the frequency characteristics of the external and middle ears have been considered.

The upper limit value calculation element 48 calculates an upper limit value $g_{max}$ using the minimum notch width $g_{x-a}$ measured by the notch width setting element 45.

The auditory filter calculation element 49 calculates a filter coefficient p of a roex (p, r) filter as follows using the minimum notch width $g_{x-a}$ measured by the notch width setting element 45 and the upper limit value $g_{max}$ calculated by the upper limit value calculation element 48. Here, a difference a between Ps(0) and Ps($g_{x-a}$) in the formula (16) is expressed by the following formula (17).

$$10\log_{10}\{Ps(0)/Ps(g_{x-a})\}=(T+x)-(T+x-a)=a \tag{17}$$

Further, the difference a is expressed by the following formula (18) from the formulas (16) and (17).

$$a=10\log_{10}[-(1-r)(2+pg_{max})\exp(-pg_{max})+prg_{max}+2(1-r)]-10\log_{10}[-(1-r)(2+pg_{max})\exp(-pg_{max})+prg_{max}+(1-r)(2+pg_{x-a})\exp(-pg_{x-a})-prg_{x-a}] \quad (18)$$

Since the value of $g_{x-a}$ is a measured value, r is $10\log_{10} r=-x$ using a coefficient x for determining the dynamic range, and a is a given constant determined by the measuring conditions, if the value of $g_{max}$ is determined, it is possible to calculate the value of filter coefficient p from the formula (18).

The following method is considered to determine the value of $g_{max}$. The value of notch width g (hereinafter referred to as "$g_t$") where the threshold of signal detection and the threshold of hearing coincide is about $g_t=0.6\sim0.7$ when measurement is made using the masker produced so that the sound pressure level per 1 Hz of a person of normal hearing is 40 dBSPL, wherein the integral of a section or an interval of $g_{max}>0.8$ rarely affects the value of the notched noise masking data Ps(g).

Accordingly, referring to the past measurement data of the auditory filter, the relationship between the value of $g_{max}$ and the value of $g_t$ is expressed by the following formula (19):

$$g_{max}=Cg_t \quad (19)$$

where the value of C is about 1.1~1.3. On the other hand, in the simplified measurement method of the present invention, since the measured value is only the notch width $g_{x-a}$, the value of the notch width $g_t$ where the threshold of signal detection and the threshold of hearing coincide is unknown. It is also known that the value of notch width $g_t$ where the threshold of signal detection and the threshold of hearing coincide varies with the dynamic range (corresponding to the value x) from the measurement result (the relationship between the notch width g and the threshold of signal detection [dBSPL]). Accordingly, it is necessary to estimate the value of $g_{max}$ from the notch width $g_{x-a}$ for each value of x, and the relationship between the value of $g_{max}$ and the value of $g_{x-a}$ is expressed by the following formula (20):

$$g_{max}=A_x g_{x-a} \quad (20)$$

where $A_x$ is a coefficient which changes in accordance with the value of x. Supposing that C=1.2 in the formula (19), the value of $g_{max}$ is calculated using the measurement result (the value of $g_t$) of two subjects of normal hearing. If the value of $A_x$ is experimentally determined from the value of $g_{max}$ and the value of $g_{x-a}$, the result shown in the following Table 3 is obtained.

TABLE 3

| xdB | a | $g_t$ | $g_{max}=1.2g_t$ | $g_{x-a}$ | $A_x=g_{max}/g_{x-a}$ |
|---|---|---|---|---|---|
| 10 | 5 | 0.29 | 0.35 | 0.111 | 3.15 |
| 15 | 5 | 0.37 | 0.44 | 0.097 | 4.54 |
| 20 | 10 | 0.46 | 0.55 | 0.146 | 3.77 |
| 30 | 10 | 0.58 | 0.70 | 0.156 | 4.49 |

In Table 3, the value of $g_t$ in x=10, 15, 20 or 30 [dB] is measured to calculate the value of $A_x$, but it is also possible to prepare the value of $A_x$ for example when x=40 or 50 [dB] in advance.

Accordingly, in the auditory filter calculation element 49, the upper limit value $g_{max}$, the minimum notch width $g_{x-a}$, the value x corresponding to the coefficient r, and the value a are entered into the formula (18) to calculate the filter coefficient p of the roex (p, r) filter. Further, the shape of auditory filter is estimated from the filter coefficients p, r.

In the auditory filter display element 50, the filter shape is displayed from the filter coefficient p and the value x corresponding to the filter coefficient r.

In this manner, the value x corresponding to the filter coefficient r is set for example at 10, 20, 30, 40, 50 [dB] and an estimated value of the filter coefficient p is found for each value, wherein as shown in FIG. 9, the shape of auditory filter is displayed using the value x as a parameter (the horizontal axis: notch width g; the vertical axis: attenuation level [dB]).

Figure 8:
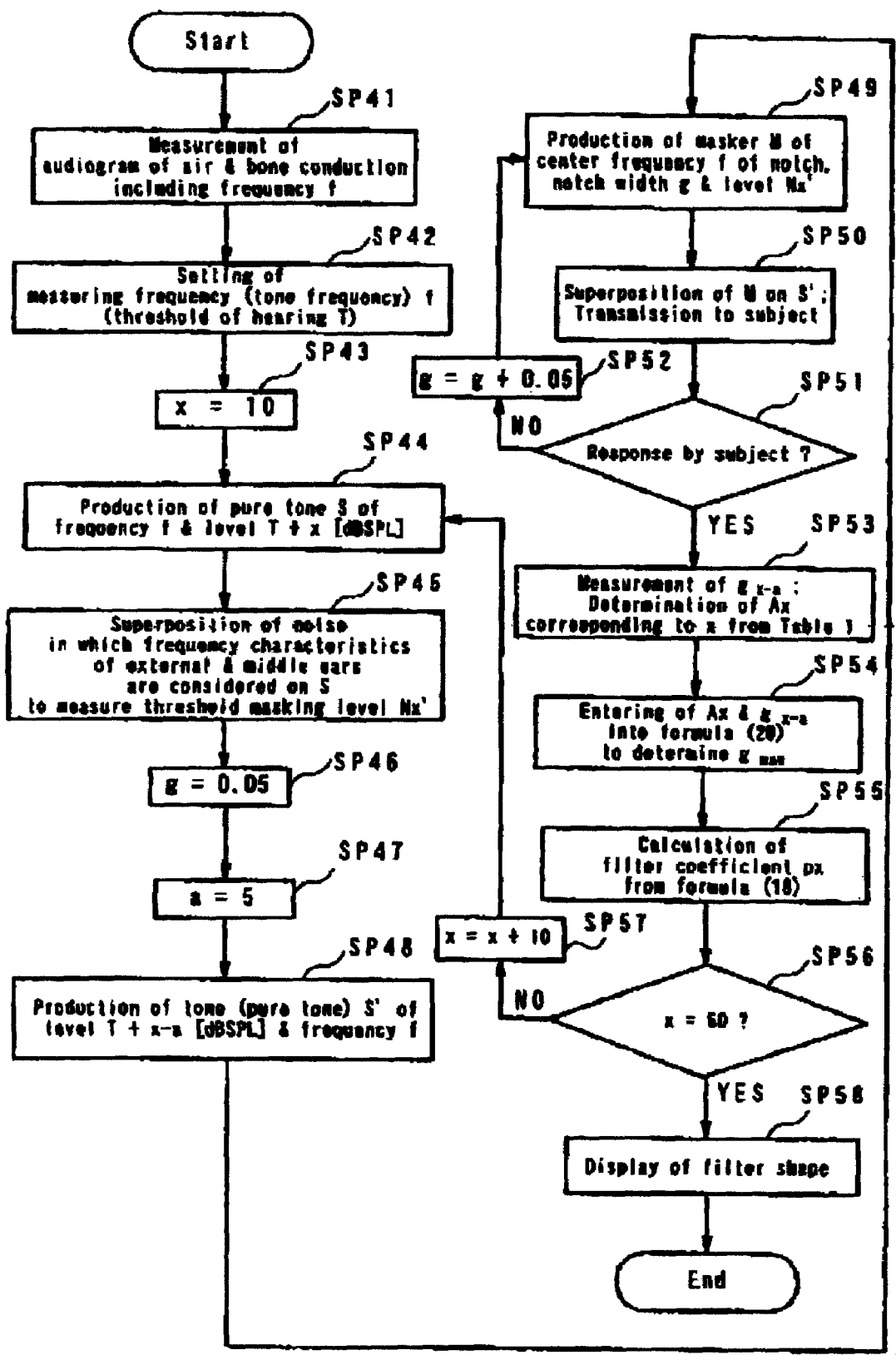
FIG. 8 is a flow chart showing the steps of a method for estimating the shape of the auditory filter according to the third embodiment of the present invention.

A method for estimating the shape of an auditory filter according to the third embodiment of the present invention will now be explained in accordance with a flow chart shown in FIG. 8.

First, in step SP 41, the audiogram of air conduction and bone conduction including a frequency f is measured in a condition where noise is not added. Here, the threshold of hearing of a pure tone in the frequency f is set at T [dBSPL]. In step SP 42, the frequency to be measured (i.e., tone frequency) f is set.

Next, in step SP 43, the value of a coefficient x for determining the dynamic range of the notched noise masking data is set. Here, x=10. In step SP 44, a pure tone S of the frequency f [Hz] and the level T+x [dBSPL] is produced.

In step SP 45, noise of which the sound pressure level per 1 Hz has been corrected to be uniform when the tone has reached the internal ear of a subject in a sufficiently low level, and noise which has been considered from a difference of the audiogram of the air and bone conduction measured in step SP 41, are superposed on the tone S. Then, the minimum level (i.e., the threshold masking level) $N_x'$ whereby the subject cannot perceive the tone S' is measured while increasing the level of this noise.

In step SP 46, the notch width g of noise of level $N_x'$ is set at a predetermined value. Here, g=0.05. Further, in step SP 47, the value a [dB] which is subtracted from level T+x [dBSPL] of the tone S is set at a predetermined value (x>a). Here, a=5

Next, in step SP 48, a pure tone S' of a frequency f [Hz] and level T+x-a [dBSPL] is produced.

In step SP 49, a masker M of which the center frequency of the notch $f_c(=f)$, the notch width g, and the level $N_x'$ is produced.

In step SP 50, the masker M is superposed on the tone S' to transmit it to a subject as an inspection sound. In step SP 51, the subject is asked to judge whether or not he can perceive the tone S' from the inspection sound. If there is no response that the subject can perceive the tone S', step SP 52 is taken. Steps SP 49~51 are repeated while gradually increasing the value of notch width g (here, increment width is set at 0.05) until a response that he can perceive the tone S' is obtained.

Now, as shown in FIG. 2, when the inspection sound is first transmitted to the subject, it is possible to set the level of the tone S' output from the tone level setting element 42 only for a predetermined time t at the start of transmission of the inspection sound. (In other words, it is possible to delay the transmission of the tone S' only for a predetermined time t after the masker M). Likewise, even in the case where a new inspection sound is transmitted to the subject after increasing the notch width g in step SP 52, it is also possible to set the level of the tone S' output from the tone level setting element 42 only for a predetermined time t at the start of transmission of the new inspection sound.

In the case where the timing of the transmission start of the tone S' and the timing of the response are remarkably different, measurement is performed again in the same conditions as before and it can be repeated until a stable response is obtained. Further, the predetermined time t does not need to be a fixed value, but it can be changed at random for each time of measurement.

In this manner, by delaying the transmission of the tone S' only for a predetermined time t after the masker M in the case of the transmission of the first inspection sound, or by suspending the transmission of only the tone S' when the value of the notch width g of the masker M is varied and transmitting to the subject the tone S' after a predetermined time t has passed, if the timing of the response by the subject at that time is observed, it is considered that the validity of response by the subject can also be judged.

As shown in FIG. 2, if there is a response indicating that the subject has perceived the tone S' after it has been transmitted to him and if the response that he has perceived the tone S' is not made at the same time as the stopping of the tone S', the response by the subject is judged to be normal. On the other hand, if there is a response that he has perceived the tone S' before it has been transmitted to him and the response that he has perceived the tone S' is maintained even after the stopping of transmission, it is possible to judge the response by the subject as abnormal. In this case, measurement is performed again or the level of the tone S' and the level of the masker M can be changed.

In step SP 51, if there is a response indicating that the subject can perceive the tone S', step SP 53 is taken.

In step SP 53, the notch width g at that time is determined as the minimum notch width $g_{x-a}$, of the subject. Further, the value of $A_x$ in the value x set above (=10 [dB]) is determined using Table 1 ($A_x$=3.15).

Then, in step SP 54, the value of $A_x$ (3.15) and the value of the minimum notch width $g_{x-a}$ measured above are entered in the formula (20) to determine the value of the upper limit value $g_{max}$ of the notch width g suitable for the subject.

In step SP 55, the measured minimum notch width $g_{x-a}$, the upper limit value $g_{max}$ of the notch width estimated from this minimum notch width $g_{x-a}$, the value x corresponding to a preset coefficient r, and the value a are entered in the formula (18) to calculate the estimated value of a filter coefficient $p_x$ (x=10) of a roex (p, r) filter.

Next, in step SP 56, it is judged whether or not x=50 is satisfied. If x=50 is not satisfied, step SP 57 is taken to have x=x+10, wherein steps SP 44~57 are repeated until x=50 is satisfied. In this manner, the estimated value of the filter coefficient $p_x$ for a new x (x=20, 30, 40, or 50 [dB]) is calculated from the formula (18). Here, the increment width of x is 10 and measurement up to x=50 is performed.

In step SP 56, when it is judged that x=50 is satisfied, the shape of auditory filter using the value x as a parameter (x=10, 20, 30, 40 or 50 [dB]) is displayed in step SP 58 as shown in FIG. 9 (the horizontal axis: notch width g; the vertical axis: attenuation level [dB]).

In the third embodiment of the present invention, as shown in FIG. 10 (a), the masker M is produced by a method for adding a notch to the noise in which frequency characteristics of the external and middle ears of the subject have been considered. However, as shown in FIG. 10 (b), this masker M can be constituted by two-band noise (of the high frequency side and the low frequency side).

Further, in the above-mentioned embodiments, it is explained that the frequency f of the tone signal output from the tone level setting elements 2, 22, 42 is caused to coincide with the center frequency $f_c$ of the masker M output from the notch width setting element 5, 25, 45. However, these do not always need to coincide, but it is sufficient that the tone signal be included within the notch width.

In the above-mentioned embodiments, in the case of finding the minimum notch width (the threshold notch width) $g_{x-a}$ which the subject can perceive, steps of setting first the notch width g of the masker M narrow (g=0.05) to transmit the inspection sound and then gradually widening the notch width g of the masker M in the case where the subject cannot perceive the tone S' from the inspection sound, to transmit the inspection sound again until he can perceive the tone S', are explained.

However, since it is sufficient if the minimum notch width $g_{x-a}$ which the subject can perceive can be found, steps for first widening the notch width g of the masker M to transmit the inspection sound so that the subject can perceive the tone S' from the inspection sound and then gradually narrowing the notch width g of the masker M to transmit the inspection sound again until he cannot perceive the tone S' can be considered.

Further, in the above-mentioned embodiments, to set the level of tone and the threshold masking level $N_x$ or $N_x'$, a so-called method of limits was explained. However, it is also possible to set these based on a psychophysical method of measurement such as two alternative forced choices for choosing either of the inspection sounds to which the tone has been added or the inspection sounds to which the tone has not been added.

Still further, in the above-mentioned embodiments, to find the minimum notch width $g_{x-a}$ which the subject can perceive, a case where a method of limits is used was explained. However, it is also possible to find the minimum notch width $g_{x-a}$ based on the psychophysical method of measurement such as two alternative forced choices.

In the above-mentioned embodiments, the filter shape was estimated by setting a model of an auditory filter as a roex (p, r) filter. However, this model function does not always need to be the roex (p, r) filter, but it can be another function (e.g., a roex (p) in which r=0 in the roex (p, r) filter) if suitable for the model of the auditory filter.

Further, in the above-mentioned embodiments, the validity of response by the subject is judged by delaying the transmission of the tone S' only for a predetermined time t afte the masker M at the start of transmission of the inspection sound in steps SP 10, SP 30, and SP 50 when measuring the minimum notch width $g_{x-a}$. It is also possible to judge the validity of the measurement of the threshold masking level $N_x$, $N_x'$ by providing the tone S' with the same delay of time as above even in the case where the level of white noise is set or changed when measuring the threshold masking level $N_x$, $N_x'$ in steps SP 5, SP 25, and SP 40.

Although there have been described what are the present embodiments of the invention, it will be understood that variations and modifications may be made thereto without departing from the spirit or essence of the disclosed invention.

What is claimed is:

1. A method for estimating the shape of an auditory filter by finding a coefficient p of a roex (p, r) filter which is used as a model for the shape of the auditory filter, comprising the steps of:

determining a threshold masking level $N_x$ based on a tone S which adds a given value x to a threshold of hearing T of a subject in frequency f;

generating a tone S' which subtracts a given value a from the tone S;

generating a masker of notch width g and a level $N_x$ including the frequency f in a notch;

transmitting to the subject an inspection sound which superposes the masker on the tone S';

measuring a minimum notch width $g_{x-a}$ of the subject while varying the notch width g;

estimating an upper limit value $g_{max}$ of the notch width g suitable for the subject from the minimum notch width $g_{x-a}$;

calculating the coefficient p from the upper limit value $g_{max}$, the minimum notch width $g_{x-a}$, the value x corresponding to a coefficient r, and a value a; and estimating the shape of the auditory filter from the coefficient p calculated above and the value x corresponding to the coefficient r.

2. The method for estimating the shape of an auditory filter according to claim 1, wherein the step of measuring the minimum notch width $g_{x-a}$ of the subject includes using the value x as a parameter.

3. The method for estimating the shape of an auditory filter according to claim 1 or claim 2, wherein when at least one of the threshold masking level $N_x$ and the minimum notch width $g_{x-a}$ is measured, transmission of the tone is started at predetermined time intervals after starting the transmission of the masker to the subject.

4. An apparatus for estimating the shape of an auditory filter by finding a coefficient p of a roex (p, r) filter which is used as a model for the shape of the auditory filter comprising:

a tone generation element for generating a tone of a predetermined frequency;

a tone level setting element for amplifying or attenuating the tone generated at the tone generation element to a predetermined level;

a noise generation element for generating noise which is not provided with a notch;

a noise level setting element for amplifying or attenuating the noise generated at the noise generation element to a predetermined level;

a notch width setting element for providing the noise with a notch including the frequency of the tone;

a notched noise superposition element for superposing the notched noise output from the notch width setting element on the tone output from the tone level setting element;

an inspection sound transmission element for transmitting to a subject an inspection sound output from the notched noise superposition element;

an upper limit value calculation element for calculating an upper limit value of the notch width suitable for the subject based on the notch width in the case where the subject can perceive the inspection sound;

an auditory filter calculation element for calculating the coefficient p of the roex (p, r) filter based on the notch width and the upper limit value thereof and for estimating the filter shape from the coefficients p and r obtained above; and an audio filter display element for displaying the filter shape estimated above.

5. The apparatus for estimating the shape of an auditory filter according to claim 4, wherein when at least one of the threshold masking level $N_x$ and the minimum notch width $g_{x-a}$ is measured, transmission of the tone is started at predetermined time intervals after starting the transmission of a masker to a subject.

6. A method for estimating the shape of an auditory filter by finding a coefficient p of a roex (p, r) filter which is used as a model for the shape of the auditory filter comprising the steps of:

generating a tone S' by subtracting a given value a from a tone S, the tone S being obtained by adding a given value x to a threshold of hearing T of a subject in a frequency f;

generating a masker of notch width g and level $N_x$ including the frequency f in a notch;

transmitting to a subject an inspection sound which superposes the masker on the tone S';

measuring a minimum notch width $g_{x-a}$ of the subject while varying the notch width g;

calculating the coefficient p from an upper limit value $g_{max}$ of the notch width g suitable for the subject from the minimum notch width $g_{x-a}$, the minimum notch width $g_{x-a}$, the value x corresponding to a coefficient r, and the value a, by applying a correction function $W_c(h)$ in which frequency characteristics in the external and middle ears of the subject are considered; and estimating the shape of the auditory filter from the coefficient p calculated above and the value x corresponding to the coefficient r.

7. The method for estimating the shape of an auditory filter according to claim 6, wherein the threshold masking level $N_x$ is determined based on the tone S which adds the given value x to the threshold of hearing T of the subject in the frequency f.

8. The method for estimating the shape of an auditory filter according to claim 6, wherein the upper Limit value $g_{max}$ of the notch width g suitable for the subject is estimated from the minimum notch width $g_{x-a}$.

9. The method for estimating the shape of an auditory filter according to claim 6, wherein when at least one of the threshold masking level $N_x$ and the minimum notch width $g_{x-a}$ is measured, transmission of the tone is started at predetermined time intervals after starting the transmission of a masker to the subject.

10. An apparatus for estimating the shape of an auditory filter by finding a coefficient p of a roex (p, r) filter which is used as a model for the shape of the auditory filter comprising:

a tone generation element for generating a tone of a predetermined frequency;

a tone level setting element for amplifying or attenuating the tone generated at the tone generation element to a predetermined level;

a noise generation element for generating noise which is not provided with a notch;

a noise level setting element for amplifying or attenuating the noise generated at the noise generation element to a predetermined level;

a notch width setting element for providing the noise with a notch including the frequency of the tone;

a notched noise superposition element for superposing the notched noise output from the notch width setting element on the tone output from the tone level setting element;

an inspection sound transmission element for transmitting to a subject an inspection sound output from the notched noise superposition element;

an auditory filter calculation element for calculating the coefficient p of the roex (p, r) filter by applying a correction function $W_c(h)$ in which frequency characteristics in the external and middle ears of the subject are considered, based on notch width and the upper limit value thereof in the case where the subject can perceive the inspection sound and for estimating the filter shape from the coefficients p and r obtained above; and an auditory filter display element for displaying the filter shape estimated above.

11. The apparatus for estimating the shape of an auditory filter according to claim 10, wherein an upper limit value calculation element for calculating an upper limit value of the notch width suitable for the subject based on the notch width in the case where the subject can perceive the inspection sound is provided.

12. The apparatus for estimating the shape of an auditory filter according to claim 10, wherein when at least one of the threshold masking level $N_x$ and the minimum notch width $g_{x-a}$, is measured, transmission of the tone is started at predetermined time intervals alter starting the transmission of a masker to the subject.

13. A method for estimating the shape of an auditory filter by finding a coefficient p of a roex (p, r) filter which is used as a model for the shape of the auditory filter comprising the steps of:

generating a tone S' by subtracting a given value a from a tone S, the tone S being obtained by adding a given value x to a threshold of hearing T of a subject in a frequency f;

generating a masker of the notch width and a level $N_x$ including in a notch the frequency f in which frequency characteristics of the external and middle ears of the subject are considered;

transmitting to the subject an inspection sound which superposes the masker on the tone S';

measuring a minimum notch width $g_{x-a}$ of the subject while varying the notch width g;

calculating the coefficient p from an upper limit value $g_{max}$ of the notch width g suitable for the subject from the minimum notch width $g_{x-a}$, the minimum notch width $g_{x-a}$, the value x corresponding to a coefficient r, and the value a; and estimating the shape of the auditory filter from the coefficient p calculated above and the value x corresponding to the coefficient r.

14. The method for estimating the shape of an auditory filter according to claim 13, wherein the threshold masking level $N_x'$ is determined based on the tone S which adds the given value x to the threshold of hearing T of the subject in the frequency f.

15. The method for estimating the shape of an auditory filter according to claim 13, wherein when at least one of the threshold masking level $N_x'$ and the minimum notch width $g_{x-a}$ is measured, transmission of the tone is started at predetermined time intervals after starting the transmission of a masker to the subject.

16. The method for estimating the shape of an auditory filter according to claim 13, wherein the upper limit value $g_{max}$ of the notch width g suitable for the subject is estimated from the minimum notch width $g_{x-a}$.

17. An apparatus for estimating the shape of an auditory filter by finding a coefficient p of a roex (p, r) filter which is used as a model for the shape of the auditory filter comprising:

a tone generation element for generating a tone of a predetermined frequency;

a tone level setting element for amplifying or attenuating the tone generated at the tone generation element to a predetermined level;

a noise generation element for generating noise which is not provided with a notch width in which frequency characteristics of the external and middle ears of a subject are considered;

a noise level setting element for amplifying or attenuating the noise generated at the noise generation element to a predetermined level;

a notch width setting element for proving the noise with a notch including the frequency of the tone;

a notched noise superposition element for superposing the notched noise output from the notch width setting element on the tone output from the tone level setting element;

an inspection sound transmission element for transmitting to the subject the inspection sound output from the notched noise superposition element;

an auditory filter calculation element for calculating the coefficient p of the roex (p, r) filter based on the notch width and the upper limit value thereof in the case where the subject can perceive the inspection sound and for estimating the filter shape from the coefficients p, r obtained above; and an auditory filter display element for displaying the filter shape estimated above.

18. The apparatus for estimating the shape of an auditory filter according to claim 17, wherein an upper limit value calculation element for calculating an upper limit value of the notch width suitable for the subject based on the notch width in the case where the subject can perceive the inspection sound is provided.

19. The apparatus for estimating the shape of an auditory filter according to claim 17, wherein when at least one of the threshold masking level $N_x'$ and the minimum notch width $g_{x-a}$ is measured, transmission of the tone is started at predetermined time intervals after starting the transmission of a masker to the subject.

* * * * *

UNITED STATES PATENT AND TRADEMARK OFFICE
CERTIFICATE OF CORRECTION

PATENT NO.       : 7,048,692 B2
APPLICATION NO.  : 10/345041
DATED            : May 23, 2006
INVENTOR(S)      : Nakaichi et al.

It is certified that error appears in the above-identified patent and that said Letters Patent is hereby corrected as shown below:

Column 1:
    Line 19, change "It is therefore considered" to --It is, therefore, considered--.
    Line 67, change "It is therefore said" to --It is, therefore, said--.

Column 2:
    Line 15, change "It is therefore an object" to --It is, therefore, an object--.
    Line 45, change "hearing aid and" to --hearing aid, and--.

Column 3:
    Line 66, change "hearing aid and" to --hearing aid, and--.

Column 4:
    Line 38, change "auditory filter comprises" to --auditory filter, comprises--.
    Line 67, change "it is there-" to --it is, there- --.

Column 5:
    Line 1, change "fore possible" to --fore, possible--.
    Line 32, change "auditory filter comprises" to --auditory filter, comprises--.

Column 6:
    Line 25, change "auditory filter comprises" to --auditory filter, comprises--.

Column 9:
    Line 64, change "setting element S" to --setting element 5--.

Column 11:
    Line 16, change "limit value g max," to --limit value $g_{max}$, --.

Column 12:
    Line 3, change "inspection sound (In" to --inspection sound. (In--.
    Line 5, change "the masker M)." to --the masker M.)--.
    Line 28, change "no such a response" to --no such response--.
    Line 65, change "step SP 18 (The" to --step SP 18. (The--.
    Line 67, change "attenuation level)." to --attenuation level.)--.

Column 15:
    Line 39, change "$(1-r)(2pg_{x-a})$ exp" to --$(1-r)(2+pg_{x-a})$exp--.

UNITED STATES PATENT AND TRADEMARK OFFICE
CERTIFICATE OF CORRECTION

PATENT NO.      : 7,048,692 B2
APPLICATION NO. : 10/345041
DATED           : May 23, 2006
INVENTOR(S)     : Nakaichi et al.

It is certified that error appears in the above-identified patent and that said Letters Patent is hereby corrected as shown below:

Column 16:
    Line 31, change "and as a result," to --and, as a result,--.

Line 60, change "$\int_{g}^{g_{max}}$" to --$\int_{0}^{g_{max}}$--.

Column 17:
    Line 45, change "in for example" to --in, for example, --.
    Line 61, change "a parameter (The" to --a parameter. (The--.
    Line 63, change "attenuation level [dB])." to --attenuation level [dB].)--.

Column 18:
    Line 39, change "to the masker M)." to --to the masker M.)--.
    Line 51, begin a new paragraph with "In this manner,".

Column 21:
    Line 66, change "cannot not perceive the tone" to --cannot perceive the tone--.

Column 22:
    Line 35, change "instructs the setting each time." to --instruct the setting each time.--.

Column 24:
    Line 38, change "Here, a=5" to --Here, a=5.--.

Column 26:
    Line 43, change "afte the masker" to --after the masker--.

Column 28:
    Line 27, change "upper Limit value" to --upper limit value--.

Column 29:
    Line 12, change "$g_{x-a}$ ,is measured, transmission" to --$g_{x-a}$ is measured transmission--.

UNITED STATES PATENT AND TRADEMARK OFFICE
CERTIFICATE OF CORRECTION

PATENT NO. : 7,048,692 B2
APPLICATION NO. : 10/345041
DATED : May 23, 2006
INVENTOR(S) : Nakaichi et al.

It is certified that error appears in the above-identified patent and that said Letters Patent is hereby corrected as shown below:

<u>Column 29 (continued)</u>:
 Line 23, change "notch width and" to --notch width g and--.

Signed and Sealed this

Eleventh Day of December, 2007

JON W. DUDAS
*Director of the United States Patent and Trademark Office*